(12) United States Patent
Shanmugasundram et al.

(10) Patent No.: US 7,534,298 B2
(45) Date of Patent: May 19, 2009

(54) APPARATUS AND METHOD OF DETECTING THE ELECTROLESS DEPOSITION ENDPOINT

(75) Inventors: Arulkumar Shanmugasundram, Sunnyvale, CA (US); Manoocher Birang, Los Gatos, CA (US); Ian A. Pancham, San Francisco, CA (US); Sergey Lopatin, Santa Clara, CA (US)

(73) Assignee: Applied Materials, Inc., Santa Clara, CA (US)

( * ) Notice: Subject to any disclaimer, the term of this patent is extended or adjusted under 35 U.S.C. 154(b) by 852 days.

(21) Appl. No.: 10/944,228

(22) Filed: Sep. 17, 2004

(65) Prior Publication Data
US 2005/0088647 A1    Apr. 28, 2005

Related U.S. Application Data

(60) Provisional application No. 60/503,833, filed on Sep. 19, 2003.

(51) Int. Cl.
*B05D 3/02* (2006.01)

(52) U.S. Cl. .................. 118/320; 118/712; 118/697; 118/52

(58) Field of Classification Search .......... 118/712, 118/602, 679, 323, 320–321, 697–699, 73, 118/52; 427/437, 438, 443.1
See application file for complete search history.

(56) References Cited

U.S. PATENT DOCUMENTS

| | | | |
|---|---|---|---|
| 3,804,638 | A | 4/1974 | Jonker et al. |
| 4,469,713 | A | 9/1984 | Zoeller |
| 4,556,845 | A | 12/1985 | Strope et al. |
| 4,695,700 | A | 9/1987 | Provence et al. |
| 4,699,081 | A | 10/1987 | Mack |
| 4,718,990 | A | 1/1988 | Sugiura |

(Continued)

FOREIGN PATENT DOCUMENTS

EP    0315386    10/1989

(Continued)

OTHER PUBLICATIONS

PCT International Search Report for PCT/US2006/000573, dated May 19, 2006.

(Continued)

*Primary Examiner*—Brenda A Lamb
(74) *Attorney, Agent, or Firm*—Patterson & Sheridan

(57) ABSTRACT

An apparatus and a method of controlling an electroless deposition process by directing electromagnetic radiation towards the surface of a substrate and detecting the change in intensity of the electromagnetic radiation at one or more wavelengths reflected off features on the surface of the substrate. In one embodiment the detected end of an electroless deposition process step is measured while the substrate is moved relative to the detection mechanism. In another embodiment multiple detection points are used to monitor the state of the deposition process across the surface of the substrate. In one embodiment the detection mechanism is immersed in the electroless deposition fluid on the substrate. In one embodiment a controller is used to monitor, store, and/or control the electroless deposition process by use of stored process values, comparison of data collected at different times, and various calculated time dependent data.

46 Claims, 12 Drawing Sheets

U.S. PATENT DOCUMENTS

| | | | |
|---|---|---|---|
| 4,851,311 A | 7/1989 | Millis et al. | |
| 4,939,370 A | 7/1990 | Kurpjoweit | |
| 5,166,525 A | 11/1992 | Rodgers et al. | |
| 5,190,614 A | 3/1993 | Leach et al. | |
| 5,308,414 A | 5/1994 | O'Neill et al. | |
| 5,499,733 A | 3/1996 | Litvak | |
| 5,536,359 A | 7/1996 | Kawada et al. | |
| 5,872,633 A | 2/1999 | Holzapfel et al. | |
| 5,958,148 A | 9/1999 | Holzapfel et al. | |
| 5,985,679 A | 11/1999 | Berman | |
| 6,081,334 A | 6/2000 | Grimbergen et al. | |
| 6,217,410 B1 | 4/2001 | Holzapfel et al. | |
| 6,395,130 B1 | 5/2002 | Adams et al. | |
| 6,406,641 B1 | 6/2002 | Golzarian | |
| 6,642,155 B1 * | 11/2003 | Whitman et al. | 438/758 |
| 6,806,948 B2 | 10/2004 | Katz et al. | |
| 6,812,478 B2 | 11/2004 | Amartur | |
| 2003/0098241 A1 | 5/2003 | Homma et al. | |
| 2003/0181040 A1 | 9/2003 | Ivanov et al. | |
| 2004/0052963 A1 | 3/2004 | Ivanov et al. | |
| 2004/0065540 A1 | 4/2004 | Mayer et al. | |
| 2004/0084143 A1 | 5/2004 | Ivanov et al. | |
| 2004/0094087 A1 | 5/2004 | Ivanov et al. | |
| 2004/0094186 A1 | 5/2004 | Ivanov | |
| 2004/0097071 A1 | 5/2004 | Ivanov | |

FOREIGN PATENT DOCUMENTS

| | | |
|---|---|---|
| EP | 0615001 A1 | 9/1994 |
| GB | 2181835 A | 4/1987 |
| JP | 61161403 | 7/1986 |
| JP | 63038579 | 2/1988 |
| JP | 63140086 | 6/1988 |
| JP | 63186872 | 8/1988 |

OTHER PUBLICATIONS

PCT International Search Report from International Application No. PCT/US2004/030444, dated Jan. 25, 2005.

Pete, Alex, "Using Laser Beam Expanders", Edmund Industrial Optics, Barrington, NJ, Oct. 2004, http://www.edmundoptics.com/techSupport/DisplayArticle.cfm?articleid=270.

"Frequently Asked Questions on Optics: Part 1", Edmund Industrial Optics, Barrington, NJ, Oct. 2004, http://www.edmundoptics.com/techSupport/DisplayArticle.cfm?articleid=284.

"Glossary—Beam Expander", Melles Griot, CVI Laser, LLC, Oct. 2004, http://www.mellesgriot.com/glossary/wordlist/glossarydetails.asp?wID=105.

* cited by examiner

APPARATUS AND METHOD OF DETECTING THE ELECTROLESS DEPOSITION ENDPOINT

CROSS-REFERENCE TO RELATED APPLICATIONS

This application claims benefit of provisional U.S. Patent Application Ser. No. 60/503,833, filed Sep. 19, 2003, entitled "Apparatus and Method of Detecting The Electroless Deposition Endpoint," and is herein incorporated by reference.

BACKGROUND OF THE INVENTION

1. Field of the Invention

The present invention generally relates to an apparatus and method of depositing a conductive material over sub-micron apertures formed on a substrate.

2. Description of the Related Art

Reliably producing sub-micron and smaller features is one of the key technologies for the next generation of very large scale integration (VLSI) and ultra large scale integration (ULSI) semiconductor devices. However, as the boundaries of circuit technology are pressed, the shrinking dimensions of interconnects in VLSI and ULSI technologies have placed additional demands on the processing capabilities and consistent uniform control of the device formation process. The multilevel interconnects that lie at the heart of these technologies requires precise processing of complex features such as single or dual damascene structures and high aspect ratio features, such as vias and other interconnects. Reliable formation of these interconnects and reliable connection of these features to other devices is very important to VLSI and ULSI success and to the continued effort to increase circuit density and device yield of individual substrates.

Semiconductor processing generally involves the deposition of material onto and removal ("etching") of material from substrates. Typical deposition processes include chemical vapor deposition (CVD), physical vapor deposition (PVD), electroplating, and electroless plating. Removal processes include chemical mechanical planarization (CMP) etching and others. During the processing and handling of substrates, the substrates undergo various structural and chemical changes. Illustrative changes include the thickness of layers disposed on the substrate, the material of layers formed on the substrate, surface morphology, changes in the device patterns, etc. These changes must be controlled in order to produce the desired electrical characteristics of the devices formed on the substrate. In the case of etching, for example, end-point detection methods are used to determine when the requisite amount of material has been removed from the substrate. More generally, successful processing requires ensuring the correct process recipe, controlling process excursions (e.g., gas flow, temperature, pressure, electromagnetic energy, duration, etc) and the like.

Currently, copper and its alloys have become the metals of choice for sub-micron interconnect technology, because copper has a lower resistivity than aluminum, (1.7 $\mu\Omega$-cm compared to 3.1 $\mu\Omega$-cm for aluminum), a higher current carrying capacity, and a significantly higher electromigration resistance. These characteristics are important for supporting the higher current densities required for the high levels of integration and increased device speed. Copper can be deposited by various techniques such as PVD, CVD and electroplating.

Typical device features utilizing copper or copper alloys are single damascene or dual damascene processes. In damascene processes, a feature is etched in a dielectric material and subsequently filled with copper. A barrier layer is deposited conformally on the surfaces of the features formed in the dielectric layer prior to deposition of the copper. Copper is then deposited over the barrier layer and the surrounding field. As layers of materials are sequentially deposited and removed, the uppermost surface of the substrate may become non-planar across its surface and require planarization. Planarizing a surface, or "polishing" a surface, is a process where material is removed from the surface of the substrate to form a generally even, planar surface. Planarization is useful in removing undesired surface topography and surface defects, such as rough surfaces, agglomerated materials, crystal lattice damage, scratches, and contaminated layers or materials. Planarization is also useful in forming features on a substrate by removing excess deposited material used to fill the features and to provide an even surface for subsequent levels of metallization and processing.

Chemical mechanical planarization, or chemical mechanical polishing (CMP), is a common technique used to planarize substrates. CMP utilizes a chemical composition, typically a slurry or other fluid medium, for selective removal of material from substrates. In conventional CMP techniques, a substrate carrier or polishing head is mounted on a carrier assembly and positioned in contact with a polishing pad in a CMP apparatus. The carrier assembly provides a controllable pressure to the substrate urging the substrate against the polishing pad. The pad is moved relative to the substrate by an external driving force. The CMP apparatus effects polishing or rubbing movement between the surface of the substrate and the polishing pad while dispersing a polishing composition, or slurry, to effect chemical activity and/or mechanical activity and consequential removal of material from the surface of the substrate.

After the surface of the substrate has been planarized the surface will generally comprise an array of exposed features and a "filed area" comprising some form dielectric material that electrically isolates the features from one another. The exposed features may contain such interconnecting metals as copper, aluminum or tungsten and barrier materials such as tantalum, tantalum nitride, titanium, titanium nitride, cobalt, ruthenium, molybdenum, etc.

Even though copper has been selected as one of the favorite interconnection materials it has a couple drawbacks, since it is difficult to etch, it has a tendency to form a stable oxide layer when exposed to the atmosphere, and can form various corrosion products when exposed to other aggressive semiconductor fabrication environments. The formation of the stable oxide layer can greatly affect the reliability of the connections. To resolve this problem, various methods have been employed to deposit a more inert metallic layer, or capping layer, over the interconnecting materials to reduce the oxidation of the surface or the subsequent attack of the exposed layers. The capping layer can be deposited by physical vapor deposition (PVD), molecular beam epitaxy (MBE), chemical vapor deposition (CVD), atomic layer deposition (ALD) or electroless deposition processes. Since PVD, CVD, ALD and MBE will indiscriminately and not selectively deposit the capping layer material across the surface of the substrate, subsequent polishing or patterning and etching will be required to electrically isolate the exposed features. The added steps of polishing, pattering and etching adds great complexity to the device forming process. Therefore, electroless deposition processes are often preferred.

Although electroless deposition techniques have been widely used to deposit conductive metals over non-conductive printed circuit boards, electroless deposition techniques have not been extensively used for forming interconnects in VLSI and ULSI semiconductors. Electroless deposition involves an autocatalyzed chemical deposition process that does not require an applied current for the reaction to occur. Electroless deposition typically involves exposing a substrate to a solution by immersing the substrate in a bath or by spraying the solution over the substrate. Deposition of a conductive material in micron technology by electroless or electroplating techniques require a surface capable of electron transfer for nucleation of the conductive material to occur over that surface. Non-metal surfaces and oxidized surfaces are examples of surfaces which cannot participate in electron transfer. Barrier layers comprising titanium, titanium nitride, tantalum, and/or tantalum nitride are poor surfaces for nucleation of a subsequently deposited conductive material layer, since native oxides of these barrier layer materials are easily formed.

One issue that arises with the use of an electroless deposition process is the effect that surface contamination or oxidation has on the time it takes the electroless deposition process to begin or "initiate." This time, often known as the "initiation time," is strongly dependent on the ability of the catalytic layer fluid or deposition fluid to interact with the surface of the interconnect feature. Once the electroless reaction has initiated, the time to deposit a defined amount of material is predictable and will generally fall into a relatively repeatable range of deposition rates. However, since if there is no way to know when the process has initiated and the initiation time varies from substrate to substrate or from one area of a substrate to another it is hard to know when the desired thickness of material has been deposited across the surface of the substrate. To compensate for this type of process variation, engineers will often use a worst case processing time to assure that a desired amount of material is deposited across the surface of the substrate or from one substrate to another. Use of a worst case process time causes the throughput of the deposition chamber to suffer and is wasteful of the often expensive electroless deposition solutions. Also, variations in thickness of the deposited film across the surface of the substrate and/or the variations substrate-to-substrate will cause variations in the processing speed (e.g., propagation delay) of the formed devices. The variation in speed of the formed devices, created by the variation in resistance (i.e., varying thickness) can have a large affect on device yield.

Therefore, there is a need for an improved apparatus and method for monitoring and detecting the endpoint of an electroless deposition process.

SUMMARY OF THE INVENTION

Aspects of the invention provide an apparatus for monitoring an electroless deposition process to determine the end of an electroless process step. The apparatus includes a chamber, a substrate support, an electromagnetic radiation source directed towards the substrate support, a detector that detects the intensity of reflected electromagnetic radiation from a surface of a substrate mounted on the substrate support, and a controller adapted to receive a signal from the detector and control the electroless deposition process.

In another aspect of the invention an apparatus for monitoring an electroless deposition comprises a chamber, a substrate support, an electromagnetic radiation source directed towards the substrate support, a detector that detects the intensity of reflected electromagnetic radiation from a surface of a substrate, a second detector that detects the intensity of the electromagnetic radiation from the electromagnetic radiation source, and a controller adapted to receive a signal from the detector and control the electroless deposition process.

In another aspect of the invention an apparatus for monitoring an electroless deposition comprises a chamber, a substrate support, an electromagnetic radiation source comprising one or more light emitting diodes directed towards the substrate support, a detector that detects the intensity of reflected electromagnetic radiation from a surface of a substrate mounted on the substrate support, and a controller adapted to receive a signal from the detector and control the electroless deposition process.

In another aspect of the invention a system for monitoring an electroless deposition comprises a chamber, a substrate support, an electromagnetic radiation source directed towards the substrate support, a detector that detects the intensity of reflected electromagnetic radiation from a surface of a substrate, a controller adapted to receive a signal from the detector, and is further adapted to control the electroless deposition process and a memory coupled to the controller. The memory comprising a computer-readable medium having a computer-readable program embodied therein for directing the operation of the electroless deposition system. The computer-readable program comprising computer instructions that are coded to start the deposition process, collect and store into the memory the intensity of the reflected electromagnetic radiation data, compare the stored data with the collected data, and then subsequently stop the electroless deposition process when the collected data exceeds a threshold value.

Aspects of the invention provide a method of controlling an electroless deposition process by positioning a substrate in an electroless deposition chamber, emitting electromagnetic radiation from a broadband light source onto the substrate, detecting an intensity of the electromagnetic radiation at one or more wavelengths that is reflected off a surface of a substrate, and monitoring the intensity of the electromagnetic radiation at the one or more wavelengths to determine the status of the electroless deposition process.

Another aspect of the invention provides a method of controlling an electroless deposition process by emitting electromagnetic radiation from a broadband light source, detecting an intensity of the electromagnetic radiation at one or more wavelengths that is reflected off a surface of a substrate, comparing the detected electromagnetic radiation intensity data collected at a first time with detected electromagnetic radiation intensity data collected at a second time, and modifying a process step when the difference between the detected electromagnetic radiation at the first time with detected electromagnetic radiation at the second time exceeds a process value.

Another aspect of the invention provides a method of controlling an electroless deposition process by emitting electromagnetic radiation from a broadband light source, detecting an intensity of the electromagnetic radiation reflected off a surface of a substrate at a first time, detecting an intensity of the electromagnetic radiation reflected off a surface of a substrate at a second time, calculating a first rate of change of the intensity using the stored electromagnetic radiation data at a first time and the data at a second time, detecting an intensity of the electromagnetic radiation reflected off a surface of a substrate at a third time, detecting an intensity of the electromagnetic radiation reflected off a surface of a substrate at a fourth time, calculating a second rate of change of the intensity using the stored electromagnetic radiation data at the third time and the data at the fourth time, comparing the calculated rate of change at the first time and the second time, and modifying the electroless deposition process when the difference between the rate of change of the intensity at the first time and the second time equals a process value.

Another aspect of the invention provides a method of controlling an electroless deposition process by emitting electromagnetic radiation from a broadband light source, detecting an intensity of the electromagnetic radiation at one or more wavelengths from the broadband light source by use of a first detector, detecting an intensity of the electromagnetic radiation at one or more wavelengths that is reflected off a surface of a substrate during an electroless deposition process by use of a second detector, calculating a difference in intensity of the detected electromagnetic radiation at the one or more wavelengths by the first detector and the second detector, and monitoring the calculated difference in intensity at one or more wavelengths over time to determine the status of the electroless deposition process.

Another aspect of the invention provides a method of controlling an electroless deposition process by delivering an electroless deposition fluid to a substrate in an electroless deposition chamber, immersing a detector in the electroless deposition fluid in contact with the substrate, detecting the intensity of the electromagnetic radiation by emitting electromagnetic radiation from a broadband light source and detecting an intensity of the electromagnetic radiation at one or more wavelengths reflected off a surface of a substrate, comparing the detected intensity of the electromagnetic radiation at a first time with a detected intensity of the electromagnetic radiation at a second time, starting a deposition timer when the difference between the intensity of the electromagnetic radiation at the first time and the intensity of the electromagnetic radiation at the second time equals a process value and modifying a process step when after the deposition timer has reached a defined period of time.

Another aspect of the invention provides a method of controlling an electroless deposition process by emitting electromagnetic radiation from a broadband light source, detecting an intensity of the electromagnetic radiation at one or more wavelengths reflected off a surface of a substrate during an electroless deposition process at two or more positions on the surface of the substrate, comparing a detected electromagnetic radiation at a position on the surface of the substrate at a first time with the electromagnetic radiation at a second time and modifying a process step when the difference between the electromagnetic radiation at the position on the surface of the substrate at a first time and a second time exceeds a process value.

Another aspect of the invention provides a method of controlling an electroless deposition process by emitting electromagnetic radiation from a light source, detecting the intensity of reflected electromagnetic radiation off a surface of a substrate by use of a detector, scanning the detector across the surface of the substrate, calculating the average state of the process by summing the monitored intensities at one or more wavelengths over a period of time and dividing the summed results by the period of time, and modifying a process step when the calculated average intensity equals some process value.

Another aspect of the invention provides a method of controlling an electroless deposition process by emitting electromagnetic radiation from a light source, detecting the intensity of reflected electromagnetic radiation off a surface of a substrate at two or more wavelengths, calculating a difference in intensity of detected electromagnetic radiation intensity values at a first time and a second time at each detected wavelength, and monitoring the intensity of the electromagnetic radiation at a wavelength that has the largest calculated difference to determine the status of the electroless deposition process.

In another aspect of the invention an apparatus for monitoring an electroless deposition comprises a chamber, a substrate support disposed in the chamber having a substrate receiving surface, a substrate having a detection feature on a surface, wherein the substrate is disposed on the substrate receiving surface of the substrate support, an electromagnetic radiation source directed towards the surface of the substrate, a detector that detects the intensity of reflected electromagnetic radiation from the detection feature during an electroless deposition process, and a controller adapted to receive a signal from the detector and control the electroless deposition process.

Another aspect of the invention provides a method of controlling an electroless deposition process by positioning a substrate in an electroless deposition chamber, emitting electromagnetic radiation from a broadband light source onto a detection feature on the substrate, detecting an intensity of the electromagnetic radiation at one or more wavelengths that is reflected off the detection feature during an electroless deposition process step by use of a detector, and monitoring the intensity of the electromagnetic radiation at the one or more wavelengths to determine the status of the electroless deposition process.

Another aspect of the invention provides a method of controlling an electroless deposition process by positioning a substrate in an electroless deposition chamber, emitting electromagnetic radiation from a broadband light source onto the substrate, detecting an intensity of the electromagnetic radiation at one or more wavelengths that is reflected off a surface of a substrate at the start of the electroless deposition process by use of a detector, detecting an intensity of the electromagnetic radiation at one or more wavelengths that is reflected off a surface of a substrate at a second time by use of a detector, and modifying a process step when the change in the detected intensity at one or more wavelengths exceed a desired level.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Figure 1A:
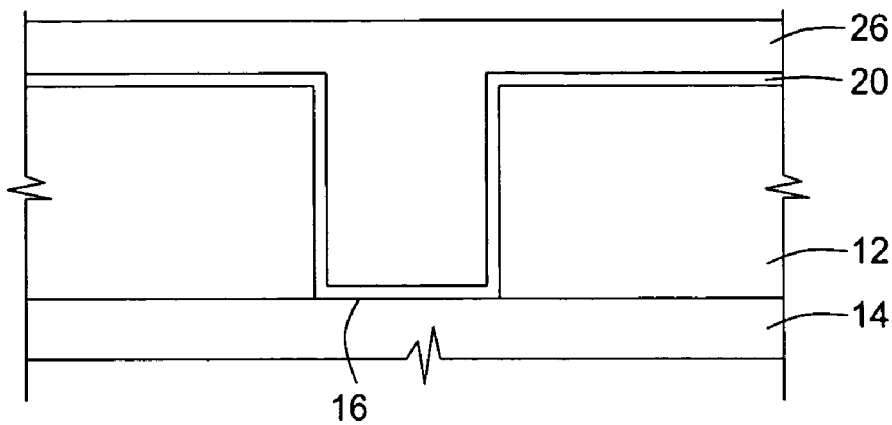
FIGS. 1A-1C shows schematic cross-sectional views of a feature processed using embodiments of the present invention.

FIG. 1A shows a schematic cross-sectional view of a substrate base 14 formed on a substrate 10 and filled by a physical vapor deposition (PVD), Chemical vapor deposition (CVD), electrochemical deposition (ECP), electroless deposition, or a molecular beam epitaxy (MBE) process. The substrate 10 refers to any workpiece upon which film processing is performed. For example, the substrate 10 may be a silicon semiconductor substrate (or wafer), or other material layer that has been formed on the substrate. A dielectric layer 12 is deposited over the substrate. The dielectric layer 12 is generally an oxide, a silicon oxide, carbon-silicon-oxide, a fluoro-silicon, a porous dielectric, or other suitable dielectric. The dielectric layer 12 is patterned to provide a feature 16, such as a via, trench, contact hole, or line extending to an exposed surface portion of the substrate base 14. It is also understood by those with skill in the art that the present invention may be used in a dual damascene process flow. The substrate 10 is used to denote the substrate base 14, as well as other material layers formed on the substrate base 14, such as the dielectric layer 12 and other subsequently deposited material layers.

Figure 1B:
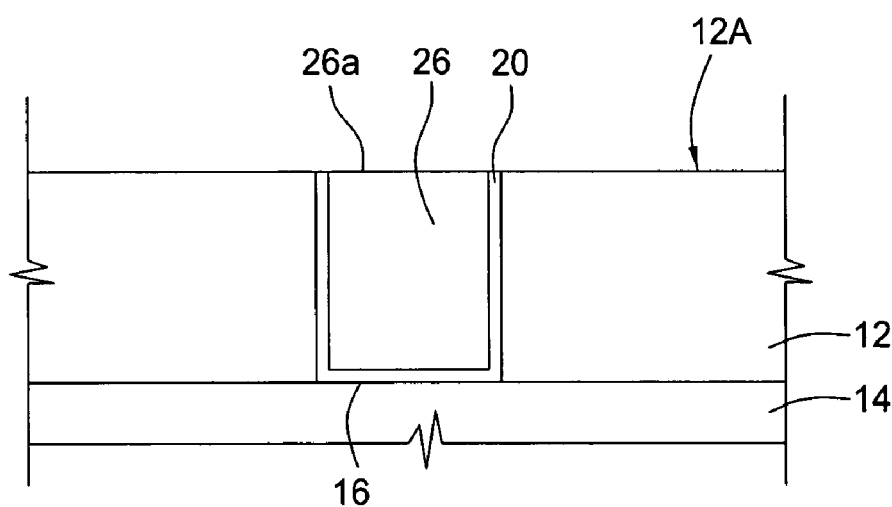
Figure 1C:
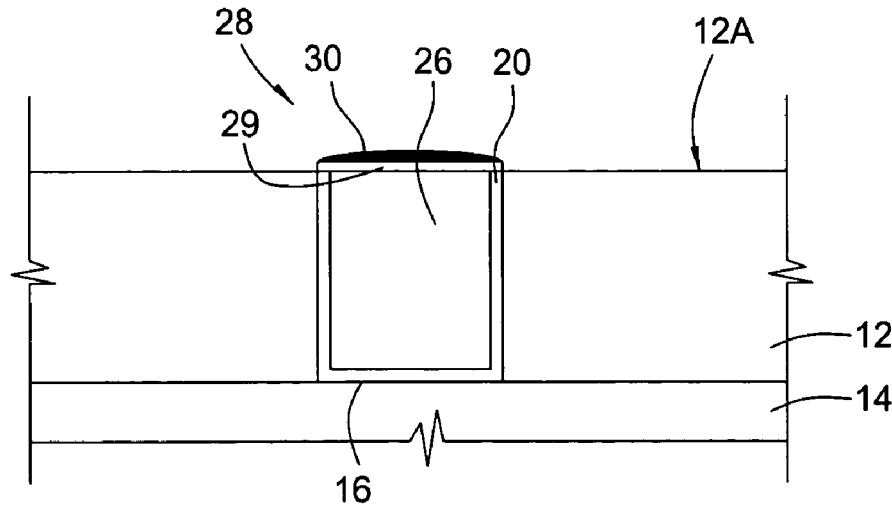

FIG. 1A shows one method of filling the feature 16 including depositing a barrier layer 20 over the substrate base 14 and filling the remaining aperture by depositing a conductive material layer 26. The conductive material layer 26 may be deposited by electroless deposition, ECP, PVD, CVD, or a combination of electroless deposition followed by electroplating, PVD, or chemical vapor deposition. Depending the shape and size of the feature 16, the process of filling the feature 16 may be more complicated than what is shown in FIGS. 1A-1C, due to other process requirements that require additional layers to be formed to fill the feature 16. An example of layers found in a more complicated device are: a barrier layer, a seed layer, a catalytic layer (if electroless), an intermediate seed layer and/or the bulk conductive layer.

FIG. 1B generally shows the next major processing step including the planarization of the top portion of the filled features, which may be completed by a process such as chemical mechanical polishing. The planarization step may also be completed by an electrochemical planarization (ECMP) process where the use of mechanical, chemical, and/or electrochemical activity is used to remove the desired materials.

Since the feature surface 26a of the conductive material layer 26 is an interface used to electrically connect the devices in the current metal layer to subsequent metal layers placed on top of the current metal layer, any oxidation or contamination on the interface can affect the ability to make contact to the current metal layer and thus affect device yield. Therefore, a capping layer 28, as shown in FIG. 1C, which does not corrode in subsequent processes or allow a thick oxide layer to form on the feature surface 26a is needed. Since PVD, MBE, CVD, and ALD deposition processes will indiscriminately and not selectively deposit the capping layer material across the surface of the substrate, subsequent polishing or patterning and etching will be required to electrically isolate the exposed devices/features. Due to its ability to selectively deposit a film, electroless deposition processes are often preferred.

In one embodiment the capping layer 28 is a single electrolessly deposited layer (not shown). The capping layer 28 may be formed on the conductive portions of the substrate surface by depositing cobalt or a cobalt alloy. For example, useful cobalt alloys include cobalt-tungsten alloys, cobalt-phosphorus alloys, cobalt-tin alloys, cobalt-boron alloys, and also alloys, such as cobalt-tungsten-phosphorus (CoWP), cobalt-tungsten-boron (CoWB), and cobalt-tungsten-phosphorus-borane (CoWPB). The capping layer 28 in this embodiment may be deposited to a thickness of about 150 Å or less, such as between about 100 Å and about 200 Å.

In another embodiment the capping layer 28 may be made up of two or more deposited layers, such as a catalytic layer 29 and a conductive cap layer 30. A very thin catalytic layer 29 is first deposited to promote adhesion of the conductive cap layer 30 to the conductive material layer 26 and the barrier layer 20. In one embodiment the catalytic layer 29 is deposited by an electroless deposition process to promote adhesion to all layers in feature 16 except the barrier layer 20. The catalytic layer may be formed on the conductive portions of the substrate surface by depositing one or more noble metals thereon. The catalytic layer solution generally provides for the deposition of a noble metal to a thickness of about 50 Angstroms (Å) or less, such as about 10 Å or less. The noble metal may be palladium, platinum, gold, silver, iridium, rhenium, rhodium, ruthenium, osmium, or any combination thereof. Preferably, the noble metal is palladium.

A conductive cap layer 30 is next deposited on the exposed catalytic layer 29 by a selective electroless deposition process. Preferably, the conductive cap layer 30 includes cobalt or a cobalt alloy. For example, useful cobalt alloys include cobalt-tungsten alloys, cobalt-phosphorus alloys, cobalt-tin alloys, cobalt-boron alloys, and also alloys, such as cobalt-tungsten-phosphorus, cobalt-tungsten-boron and cobalt-tungsten-phosphorus-borane. The conductive cap layer may also include other metals and metal alloys, such as nickel, tin, titanium, tantalum, tungsten, molybdenum, platinum, iron, niobium, palladium, nickel cobalt alloys, doped cobalt, doped nickel alloys, nickel iron alloys, and combinations thereof. The conductive cap layer may be deposited to a thickness of about 150 Å or less, such as between about 100 Å and about 200 Å. The method and apparatus to deposit the capping layer is more fully described in the co-pending application U.S.

patent application Ser. No. 10/284,855 [AMAT 7081], entitled "Post Rinse To Improve Selective Deposition Of Electroless Cobalt on Copper For ULSI Application" filed on Oct. 30, 2002 which is incorporated by reference herein to the extent not inconsistent with the claimed aspects and disclosure herein. The electroless deposition process steps incorporated by reference generally include the following process steps: pre-rinse, initiation layer deposition, rinse step, cap layer deposition, and post-cap layer deposition cleaning process. The pre-rinse step is designed to remove metal oxides or other contaminants on the substrate surface. "Substrate surface," as used herein, refers to a layer of material that serves as a basis for subsequent processing operations that may contain any part of an interconnect feature (feature 16), such as a plug, via, contact, line, wire, etc., and one or more nonconductive materials (dielectric layer 12), such as silicon, doped silicon, germanium, gallium arsenide, glass, and sapphire, for example. The pre-rinse process may utilize an acidic solution, preferably 0.5 wt. % of HF, 1M nitric acid and the balance DI water at about 25° C., to remove/etch a top portion (e.g., about 10 Å to about 50 Å) of the substrate surface. The pre-rinse process further includes a DI water rinse step to remove any remaining pre-rinse solution, any etched materials and particles, and any by-products that may have formed during the prior pre-rinse steps. Following the pre-rinse process, an initiation layer is deposited on the substrate surface by selectively depositing about 50 Å or less of a noble metal, such as palladium, on the exposed conductive materials of the substrate surface. In one aspect, the initiation layer is deposited from an electroless solution containing at least one noble metal salt and at least one acid. A concentration of the noble metal salt within the initiation layer electroless solution should be between about 80 parts per million (ppm) and about 300 ppm. Exemplary noble metal salts include palladium chloride ($PdCl_2$), palladium sulfate ($PdSO_4$), palladium ammonium chloride, or combinations thereof. A rinsing process using a rinsing agent, such as deionized water, for example, is applied to the substrate surface to remove any solution used in forming the initiation layer. A passivation layer is next deposited on the exposed initiation layer by a selective electroless deposition process. Preferably, the passivation layer includes cobalt or a cobalt alloy deposited using a cobalt electroless solution containing 20 g/L of cobalt sulfate, 50 g/L of sodium citrate, 20 g/L of sodium hypophosphite, and a sufficient amount of potassium hydroxide to provide a pH of about 10. Following the passivation layer deposition, the substrate surface may be cleaned to remove unwanted portions of the passivating material by use of post-deposition cleaning process. A post-deposition cleaning solution may include, for example, a solution of sulfuric acid and DI water.

In another embodiment the chemistry for the electroless catalytic layer 29 and cap layer 30 deposition processes is supplied by a manufacturer such as, for example, Enthone, Inc., West Haven, Conn. One example of a typical catalytic layer 29 deposition chemistry used is the E-CoWP Activator 763-45 (palladium (Pd)) supplied by Enthone Inc. An exemplary catalytic layer deposition process using the E-CoWP Activator 763-45 chemistry is a 25 second room temperature deposition process which will deposit about 30 Angstroms of palladium (Pd). After depositing the catalytic layer 29 using the E-CoWP Activator 763-45 chemistry, a post deposition rinse agent, Cap Chelating Rinse 5×, for example, is used to activate the catalytic layer for subsequent cap layer 30 deposition. Next the ENCAP CoWP763-38A and ENCAP CoWP763-39B cap layer 30 chemistry, mixed to manufacturer's suggested proportions, is then used to deposit about 150 Angstroms of a CoWP cap layer on the activated catalytic layer 29. An exemplary capping layer deposition process using the two part ENCAP CoWP763-38A and CoWP763-39B chemistries is a 45 second and 75 degrees Celsius deposition process to deposit about 150 Angstroms of CoWP.

In another embodiment a self-initiating capping layer chemistry from Enthone Inc. is used to cap the feature surface 26a. An example, of a typical deposition chemistry is a two part CAPB764-75A and the CAPB764-75B chemistry supplied by Enthone Inc. The two part CAPB764-75A and the CAPB764-75B chemistry is mixed to manufacturer's suggested proportions, to deposit about 150 Angstroms of a CoWB capping layer. An exemplary process utilizing the two part CAPB764-75A and the CAPB764-75B chemistry is a 45 seconds and 65 degrees Celsius deposition process to deposit a 150 Angstrom CoWB film. A pre-clean solution CAPB cleaner, supplied by Enthone, is used prior to depositing the capping layer to remove any oxides from the feature surface 26a and prepare it for the subsequent deposition.

The method of electroless deposition of a catalytic layer and/or the method of electroless deposition of a conductive material layer may be performed in any chamber adapted to contact a substrate with a processing solution, such as electroless deposition chambers, electroplating chambers, etc. In one embodiment, the catalytic layer and the conductive material layer may be deposited in the same chamber. In another embodiment, the catalytic layer and the conductive material layer are deposited in separate chambers. In one aspect, depositing the catalytic layer and the conductive material layer in separate chambers reduces the generation of particles that may form and deposit on chamber components as a result of the reaction of the catalytic layer solutions and the conductive material layer solutions.

One issue that arises with the use of an electroless deposition process is the effect that even small amounts of surface contamination or oxidation have on the time it takes the electroless deposition process to "initiate" or begin depositing material. The time it takes the electroless deposition process to initiate, or the initiation time, can vary from substrate to substrate or from one area of the substrate to another. Variation in initiation time make it hard to know how much material has been deposited at any given instant of time or when a desired amount has been deposited. The variations in initiation time, as noted above, can be wasteful of the very expensive deposition solution(s), cause variations in device performance across the substrate and substrate-to-substrate, and can reduce the substrate throughput through the electroless deposition chamber. Also, to achieve a high throughput (substrates per hour) through the electroless deposition chamber the process times to deposit thin films may be very short, for example, about 10 seconds, therefore the need to monitor and control the electroless deposition process can be critical to the creation of devices with consistent device properties. In some cases extended exposure to one or more of the electroless deposition chemistry components will cause significant corrosion of one or more of the exposed substrate surfaces. Therefore, in one aspect of the invention it is important to find a way to minimize the exposure time of the surfaces to the one or more electroless deposition chemistry components to prevent any significant corrosion from occurring.

Therefore, one of the goals of the present invention is to develop a way to monitor and/or detect the point at which a desired thickness of material has been deposited on the surface of the substrate. In general the present invention can be used to detect and monitor changes due to a change in some physical characteristic of the feature surface 26a or the deposition of a desired material. The ability to monitor, store, and manipulate the collected to data by a chamber controller can reduce the substrate-to-substrate variability and also reduce the amount of waste of the expensive deposition chemicals. Another possible goal of the present invention is a method of detecting and delivering data regarding the thickness of a deposited layer across the surface of a substrate as a function of time.

Figure 2A:
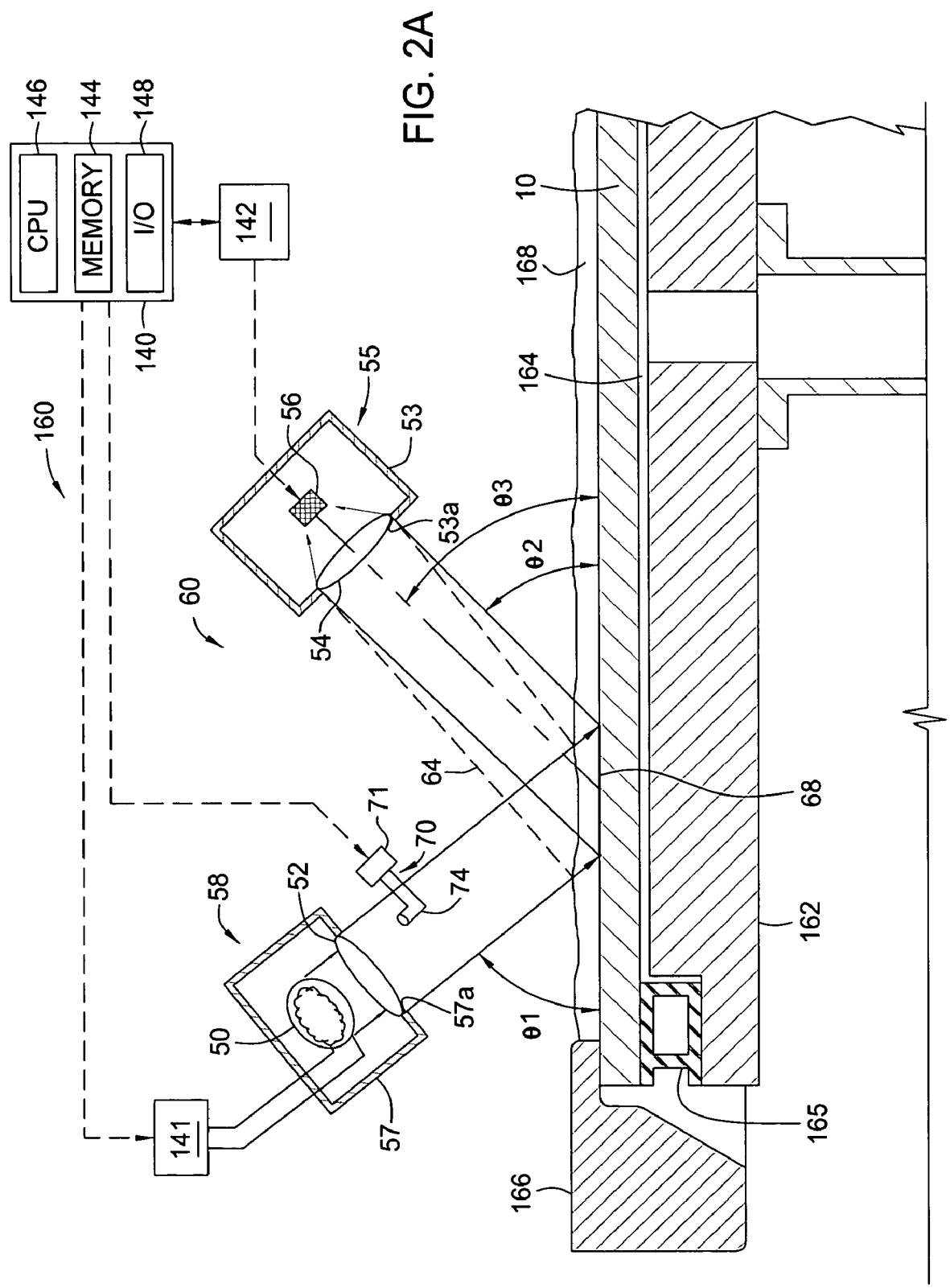
FIG. 2A shows a schematic cross-sectional view of an embodiment of a wafer detection system.

FIG. 2A shows one embodiment of the present invention that uses a detection mechanism 60 to monitor and feedback the state of the electroless deposition process as a function of time. To complete this goal the detection mechanism 60 is mounted in an electroless deposition chamber and is positioned such that it can monitor a change in the optical properties of the feature surface 26a during the electroless deposition process (e.g., catalytic layer deposition process, conductive cap layer deposition process, pre-rinse steps, rinse step, or post-cap layer cleaning process steps). In one embodiment of the present invention the electromagnetic radiation emitted from a broadband light source 58 must pass through a deposition fluid, be reflected off the features on the surface of the substrate 10, pass through deposition fluid 168, and then be collected by a detector system 55. One issue that arises when the light source and detector are positioned above the surface of the deposition fluid 168, is the light emitted from the broadband light source 58 can be reflected off the surface of the fluid and be collected by the detector system 55, thus giving a false high intensity readings at the detector. The interference caused by the reflection from the surface of the fluid (i.e., reflection 64) and other outside sources of radiation are commonly referred to as noise. In an effort to quantify the amount of noise relative to the delivered signal it is common to use a quantity known as the signal-to-noise ratio. The larger the signal-to-noise ratio the easier it is to separate the true signal from the unwanted noise present in the detection system, and thus the more confidence one can have in the collected data.

The surface of the substrate 10, as noted above, comprises the top surface of the filled features containing the conductive layer and barrier layer, and a dielectric material 12. The light projected on to the surface of the substrate 10 by the broadband light source 58 will generally only be reflected from the exposed metal surfaces and not from the dielectric layer. Given the current state of technology it is believed that the exposed metal surfaces on the surface of the substrate after the planarization step will generally account for about 50% of the total surface area of the substrate (i.e., feature density). To maximize the intensity of the radiation collected by the detector system 55, the viewing angle $\theta_3$ of the detector is preferably in-line with the radiation reflected from the surface of the substrate. The desired viewing angle $\theta_3$ can depend on the condition of the surface reflecting the light which may be affected by, for example, the surface roughness (affecting specular or diffuse reflection), refractive index of materials, and absorbing properties of the surface at an emitted wavelength. The magnitude of the desired viewing angle $\theta_3$ is commonly set to the angle equal to the angle of incidence $\theta_1$ and reflection angle $\theta_2$.

FIG. 2A shows a schematic cross-sectional view of one embodiment of a detection mechanism developed to monitor and detect the endpoint and/or growth of the deposited film. The detection mechanism 60 includes a broadband light source 58, source controller 141, a detector system 55, and a detector controller 142, and a system controller 140. The detection mechanism 60 is generally positioned a distance away from the substrate 10 such that the detector system 55 will collect and measure the intensity radiation at various wavelengths emitted by broadband light source 58 and reflected from the surface of the substrate 10. In one embodiment the broadband light source 58 will generally contain a housing 57, a light emission source 50 and an optical focusing means 52. In another embodiment the broadband light source 58 contains a light emission source 50 and a housing 57. The housing 57 encloses the light emission source 50 and allows the emitted light to pass through a single opening 57a to reduce the amount stray light that can affect the signal-to-noise ratio of the detector. The housing 57 also acts as black body to contain and emit the radiation generated from the light emission source 50. The optical focusing means 52 can be a lens or other device that collimates, focuses and/or directs the electromagnetic radiation emitted from the light emission source 50 to a viewing area 68 on the surface of the substrate 10. In one embodiment, the electromagnetic radiation from the broadband light source 58 is collected by a fiber optic cable (not shown) and transmitted to the viewing area 68, thus allowing the broadband light source 58 to be positioned a distance away from the point at which the light is to be projected onto the surface of the substrate.

Figure 4:
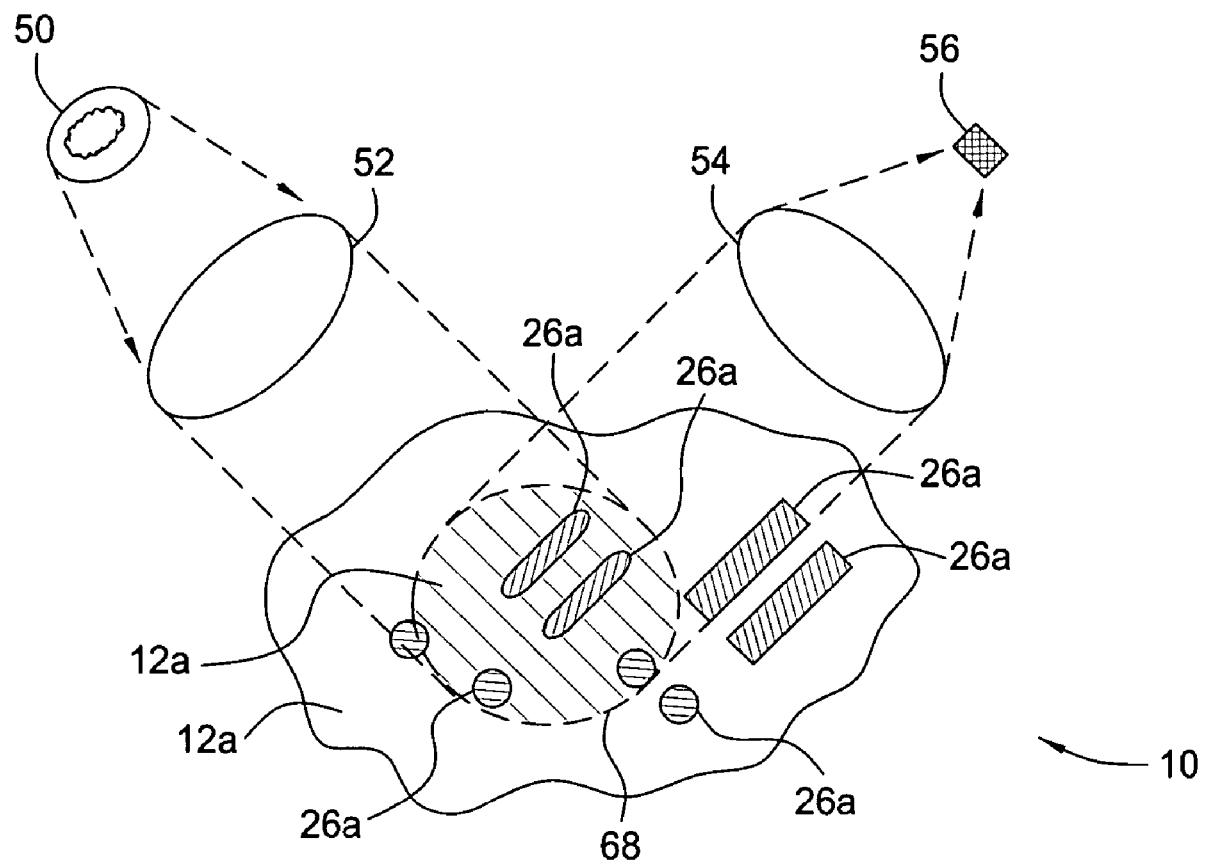
FIG. 4 shows a schematic diagram of the viewing area of a detection mechanism on a substrate surface.

FIG. 4 shows a top view of the substrate 10 after the planarization process to illustrate a viewing area 68, which contains the feature surface 26a and field surface 12a. The viewing area 68, or the area on the surface of the substrate on which the radiation is projected, is a process variable that can be adjusted to deliver the desired granularity to determine the state of the substrate surface. The variance in the signal received when using a smaller viewing area may be larger than the variance seen when using a larger viewing area due to the reduced area to average the results over. In one embodiment the viewing area may be as large as the complete surface area of the substrate. In another embodiment the viewing area may be as small as about 1 to about 2 millimeters in diameter. In another embodiment the preferred viewing area diameter is about 2 to about 50 micrometers (μm). The correlation of the reflected radiation, or signal, at a particular wavelength to the change in a process parameter, transition to a new phase of the process, or variation in surface properties of different substrates (e.g., feature density, exposed materials, etc.), can be completed by characterization of the intensity signal with the growth of the deposited film by use of one or more test pieces prior to running the desired deposition process.

The light emission source 50 is a source of electromagnetic radiation that emits a broad spectrum of radiation across the range of wavelengths from about 200 nanometers (nm) to about 800 nm. Examples of possible electromagnetic radiation sources (broadband sources) might be a tungsten filament lamp, laser diode, xenon lamp, mercury arc lamp, metal halide lamp, carbon arc lamp, neon lamp, sulfur lamp or combination thereof. In one embodiment one or more light-emitting diodes (LEDs) can be used as a electromagnetic radiation source. Light emitting diodes have some benefits over other designs since they can deliver an intense light at a very narrow range of wavelengths and they are relative inexpensive to replace if they become damaged. The use of one or more LEDs will also reduce the detection system complexity since it eliminates the need for a spectrometer, a monochromator, diffraction gratings, optical filters or other similar hardware.

The source controller 141 controls the output intensity of the light emission source 50 and delivers an output signal to the main system controller 140. In one embodiment the source controller 141 is adapted to act as a monochromator that can deliver a single spectral line from the broadband (multi-wavelength) light emission source 50. In this embodiment the source controller 141 is designed such that it can sweep the range of emitted wavelengths from the broadband light emission source as a function of time via commands sent by the main system controller 140. The use of the source controller 141 as a monochromator allows various wavelengths to be scanned as a function of time to monitor and control the electroless process.

The detector system 55 includes an electromagnetic radiation detector 56, a detector housing 53, an optical focusing means 54, and a detector controller 142. The housing 53 encloses and preferentially allows light emitted from the broadband light source 58 and reflected from the substrate 10 to be collected by the electromagnetic radiation detector 56. The electromagnetic radiation detector 56 is a detector configured to measure the intensity of electromagnetic radiation across one or more wavelengths. The electromagnetic radiation detector 56 may be selected from the following classes of sensors, for example, a photovoltaic, a photoconductive, a photoconductive-junction, a photoemissive diode, a photomultiplier tube, a thermopile, a bolometer, a pyroelectric sensor or other like detectors. In one embodiment a photoconductive detector, from Hamamatsu Photonics Norden AB, of Solna, Sweden or PLC Multipoint Inc. of Everett Wash., is used to detect a broad spectrum of the electromagnetic radiation.

In one embodiment of the present invention one or more optical filters (not shown) are added to the detector system 55, between the substrate surface and the electromagnetic radiation detector 56. The added optical filter(s) are selected to allow only certain desired wavelengths to pass to the electromagnetic radiation detector 56. This embodiment helps reduce the amount of energy striking the detector which can help improve the signal to noise ratio of the detected radiation. The optical filter(s) can be a bandpass filter, a narrowband filter, an optical edge filters, a notch filter, or a wideband filter purchased from, for example, Barr Associates, Inc. of Westford, Mass. or Andover Corporation of Salem, N.H. In another aspect of the invention an optical filter may be added to the broadband light source 58 to limit the wavelengths projected onto the substrate surface and detected by the detector system 55.

Figure 5:
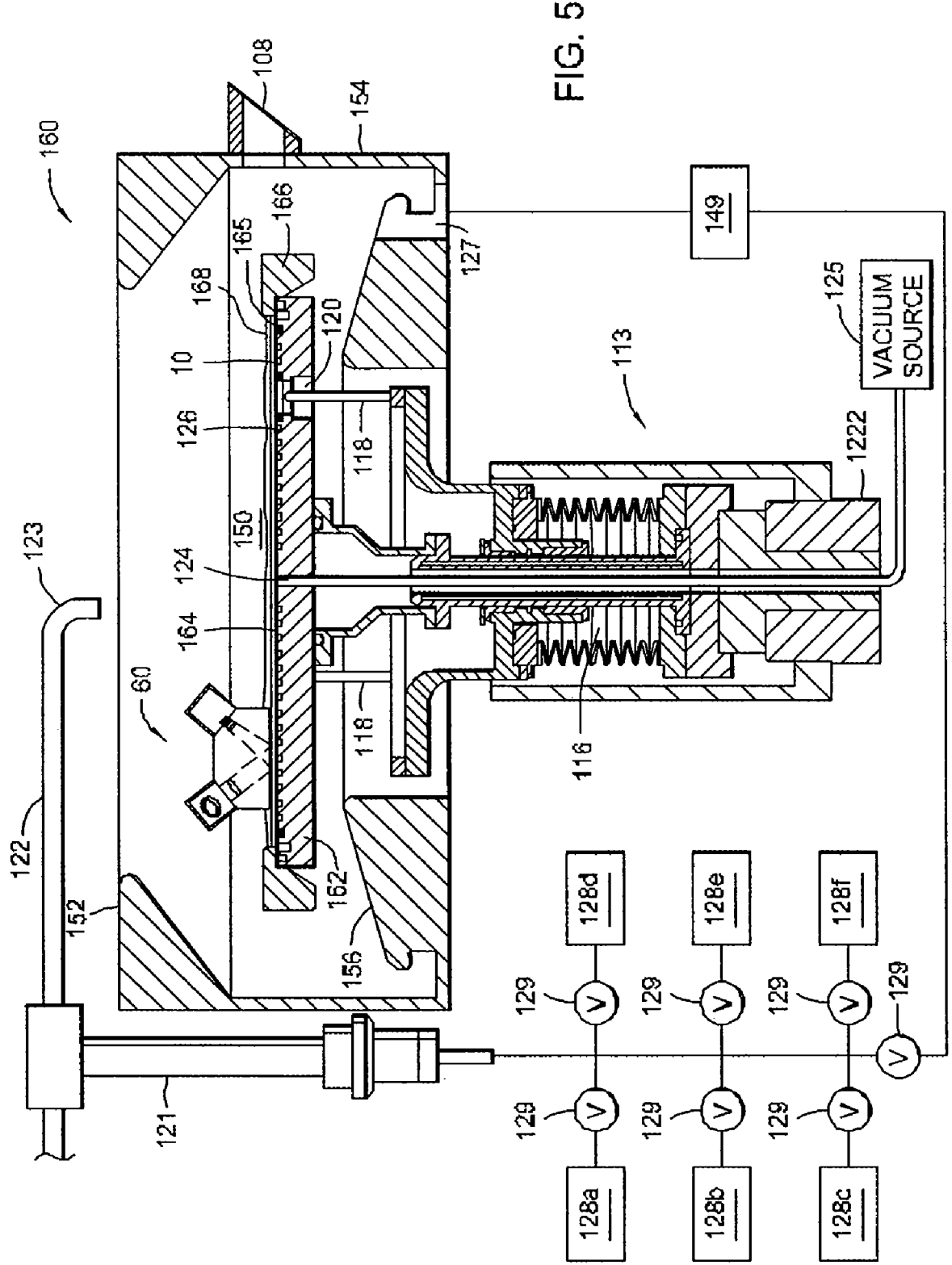
FIG. 5 shows a schematic cross-sectional view of face-up electroless processing chamber used with the present invention.
Figure 5A:
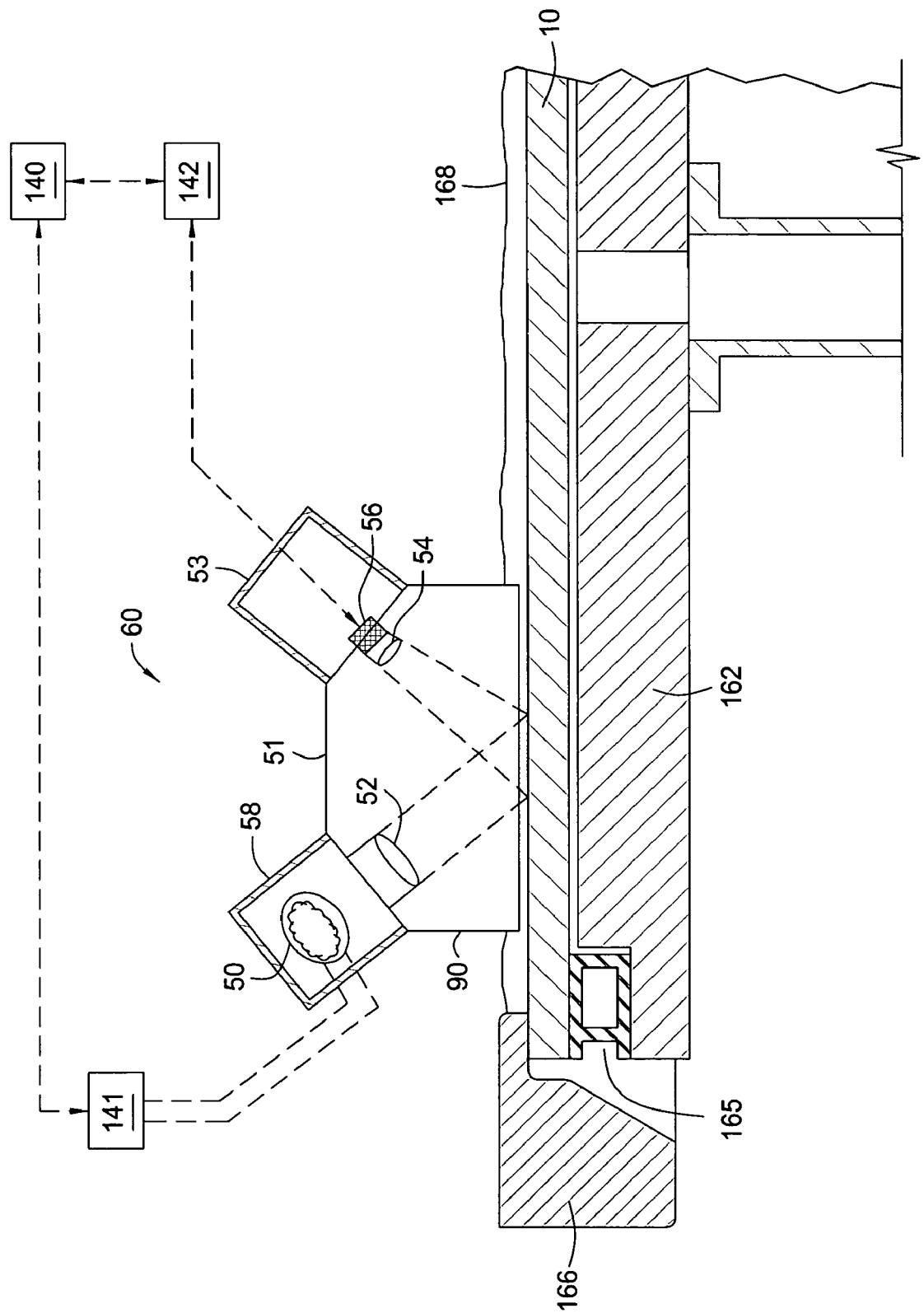
FIG. 5A a close up view of the FIG. 5 showing an embodiment of the present invention.

FIG. 5A shows a cross-sectional view of one embodiment of the invention that can reduce the affect of reflected light from the surface of the deposition fluid by immersing a transmissive body 90 in the deposition fluid. In this embodiment the broadband light source 58 and the detector system 55 are mounted on the transmissive body 90. The transmissive body 90 is incorporated in to the system to reduce noise created by the reflection the radiation off the fluid surface. While the transmissive body 90 has a solid/liquid interface, which can reflect the emitted radiation, the amount of reflected radiation can be minimized if the index of refraction difference between the transmissive body 90 and deposition fluid 168 is minimized.

In another embodiment of the present invention, the wavelength of the projected radiation projected through the deposition fluid does not affect the deposition process (e.g., photosensitive components in fluid, etc.). In the same way it is generally preferred that the emitted wavelengths are not absorbed by components in the fluid and thus affect the signal-to-noise ratio of the detected signal.

The optical focusing means 54 can be a lens or other device that collects, focuses and/or directs the electromagnetic radiation that passes through the opening 53a in the housing 53, as shown in FIG. 2A. In one embodiment a fiber optic cable (not shown) is used to collect the light reflected from the surface of the substrate and delivers it to the detector 56 that is spaced a distance away from the surface of the substrate. In one embodiment a fiber optic cable (not shown) contains and optical focusing means to collect the reflected electromagnetic radiation. In another embodiment the fiber optic cable (not shown) is placed between the optical focusing means 54 and the detector 56, thus allowing the optical focusing means to collect the maximum amount of radiation and allow the detector 56 and any associated electrical components to be remoted from the substrate processing area. The detector controller 142 is generally used to sense the output of the detector 56 and deliver an output signal to the main system controller 140.

Figure 2B:
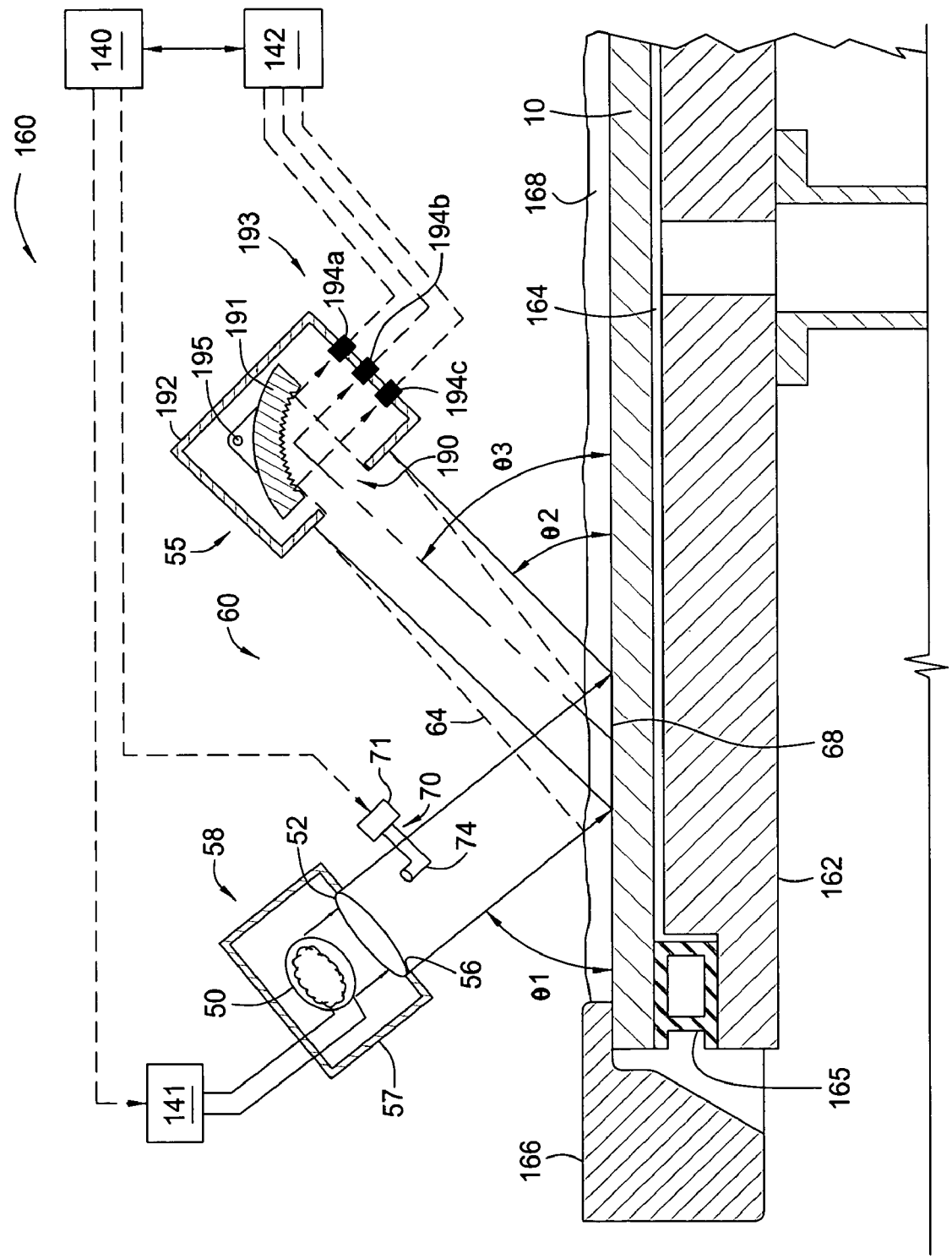
FIG. 2B shows a schematic cross-sectional view of an embodiment of a wafer detection system.

FIG. 2B illustrates one embodiment of the detection mechanism 60 in which the detector system 55 is adapted to form a spectrometer 192. A spectrometer is used to collect the radiation from a broadband light source 58, split the radiation into discrete wavelengths, and detect the intensity of the radiation at each discrete wavelength. The spectrometer typically includes an input slit 190, a diffraction grating 191 (or optical prism), a diffraction grating controller 195 and a detector array 193 to collect the incoming radiation. The diffraction grating controller 195 allows the detector controller 142 to adjust the position of the diffraction grating to control the intensity of each wavelength detected by the discrete detectors 194a-194c in the detector array 193. In one embodiment the spectrometer, is used to scan across a range of wavelengths of the emitted radiation as a function of time to monitor and control the electroless process.

In another embodiment an emission sensor 70 is incorporated into the detection system 60 so that the output of the broadband light source 58 can be measured and compared with the reflected radiation collected by the detection system 55 to enhance the detection of changes in the intensity of the reflected radiation. The emission sensor 70 senses and delivers the intensity of the radiation across a range of wavelengths to the system controller 140. The measurement of the radiation emitted from the broadband light source 58 can be accomplished by use of a fiber optic cable 74 which collects the radiation from the source and delivers it to an emission sensor detector 71. In one embodiment emission sensor detector 71 is coupled to a monochromator to collect the intensity at discrete wavelengths. In another embodiment the emission sensor 70 may be a spectrometer.

In another embodiment of the emission sensor 70 the fiber optic cable 74 collects the emitted radiation from the broadband light source 58 and delivers the collected radiation to the detection system 55. In this embodiment the light received and transferred by the fiber optic cable 74 and the radiation collected by optical focusing means 54, of the detection system 55, is selectively sensed by the detector 56 by use of a mechanical actuated slit (not shown) that is used to select the source of radiation to be detected. In this embodiment the mechanical actuated slit, which is controlled by the source controller 141 or system controller 140, first allows the intensity of the radiation received and transferred by the fiber optic cable 74 to strike the detection system 55 while preventing the radiation collected by the optical focusing means 54 from being sensed by the detection system 55. After the intensity data at one or more wavelengths has been collected from the fiber optic cable 74 the mechanical actuated slit moves to a second position. The second position of the mechanical actuated slit allows the signal collected by the optical focusing means 54 to be sensed by the detection system 55, while preventing the radiation from the fiber optic cable 74 from being sensed by the detection system 55. The order in which the two different signals are measured may be changed as needed to enhance the detection process. In another embodiment the radiation collected by the fiber optic cable 74 and the light collected by optical focusing means 54 are selectively sensed by a spectrometer 192 by use of an actuated slit that is used to selects the source of radiation to be detected.

Figure 3A:
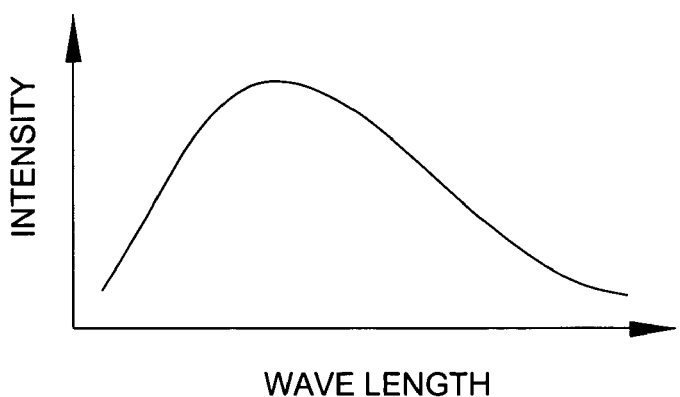
FIG. 3A illustrates a plot of intensity versus wavelength measured by the emission sensor detector.
Figure 3B:
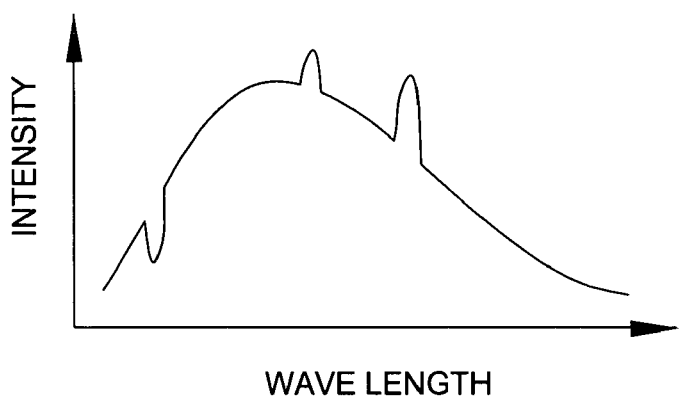
FIG. 3B illustrates a plot of intensity versus wavelength measured by the detector.
Figure 3C:
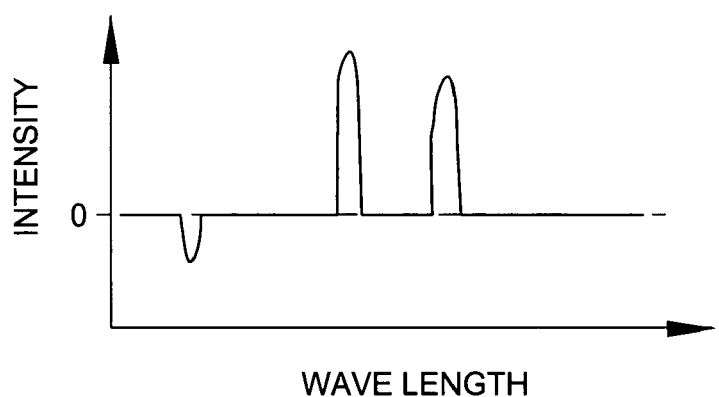
FIG. 3C illustrates a plot of intensity versus wavelength of a normalized signal created by comparing results shown in FIGS. 3A and 3B.

FIG. 3A shows an example of the intensity of the signal (or amplitude of the signal) detected by the emission sensor detector 71 as a function of wavelength. FIG. 3B shows an example of the intensity of a signal detected by the detector 56 as a function of wavelength. FIG. 3C shows the effect of dividing the intensity values of the input values sensed by the emission sensor detector 71 and the signal sensed by the detector 56, referred to as a normalized signal. The normalized signal can be created by the system controller 140 by dividing the intensity of the signals received from the emission sensor detector 71 and the detector 56 at each wavelength. In one embodiment the system controller 140 is designed to collect and save the input data from the various sensors, compare the input values to obtain the normalized signal and then take some action (e.g., continue to monitor the process, stop the process, save the data to a file, etc.) based on the normalized signal data. In another embodiment the system controller 140 compares the normalized signal at one or more wavelengths at one time with a normalized signal at some second time to decide if some action should be taken. In yet another embodiment the system controller 140 uses the intensity versus wavelength data collected from the detector 56 at time $t_1$ with the intensity versus wavelength data collected from the detector 56 at time $t_2$ to decide if some action should be taken due to changes (or lack thereof) in the intensity at one or more defined wavelengths. In yet another embodiment the intensity versus wavelength data collected from the detector 56 at time $t_1$ is subtracted from the intensity versus wavelength data collected from the detector 56 at time $t_2$ to magnify the variation from time $t_1$ and time $t_2$ at one or more wavelengths.

The controller 140 is generally designed to facilitate the control and automation of the overall system and typically may includes a central processing unit (CPU) 146, memory 144, and support circuits (or I/O) 148. The CPU 146 may be one of any form of computer processors that are used in industrial settings for controlling various chamber processes and hardware (e.g., detectors, motors, fluid delivery hardware, etc.) and monitor the system and chamber processes (e.g., chamber temperature, process time, detector signal, etc.). The memory 144 is connected to the CPU 146, and may be one or more of a readily available memory, such as random access memory (RAM), read only memory (ROM), floppy disk, hard disk, or any other form of digital storage, local or remote. Software instructions and data can be coded and stored within the memory 144 for instructing the CPU 146. The support circuits 148 are also connected to the CPU 146 for supporting the processor in a conventional manner. The support circuits 148 may include cache, power supplies, clock circuits, input/output circuitry, subsystems, and the like. A program (or computer instructions) readable by the controller 140 determines which tasks are performable on a substrate. Preferably, the program is software readable by the controller 140 and includes code to generate at least substrate positional information, spectrum from a detector 56 and an emission sensor 70, intensity and wavelength information versus substrate position information, normalized signal data, intensity and wavelength data as a function of time, calibration information and any combination thereof.

The controller 140 compares the intensity of the detected radiation at one or more wavelengths to determine the state of the electroless deposition process step and according to programmed instructions will modify the electroless deposition process step as required. The term electroless deposition process step is generally meant to encompass the various steps or phases of the electroless deposition process which may include, for example, a catalytic layer deposition process, a conductive cap layer deposition process, a pre-rinse step, a rinse step, a post-cap layer or a cleaning process steps. The term modify the electroless deposition process step is meant to generally describe an action that the controller 140 takes to assure the electroless deposition process step is performed as desired. Typical actions which the controller 140 may complete to modify an electroless deposition process step may include, for example, rinsing the substrate surface, continue to monitor the detected intensity, drying the surface of the substrate, starting a process timer, ending the electroless deposition process step, warning the user, storing the intensity at one or more wavelengths and other process data in a memory location in the controller, or waiting until a monitored electroless deposition process variable reaches some user defined process value and then taking some action. As noted above by use of a monochromator or spectrometer, intensity results at a particular wavelength on a particular area on the surface of the substrate at particular instant in time can be singled out and compared with intensity results measured in the same area on the surface of the substrate at the same wavelength at a second instant in time. The selection of which wavelengths should be monitored to detect the initiation of the electroless deposition process, the end of a processing step or electroless deposition process endpoint is dependent on the electroless process type (e.g., catalytic layer deposition, cap layer deposition, etc.), the thickness of the deposited film, and/or the type of materials present on the substrate 10 (e.g., dielectric layer material, dielectric layer thickness, barrier material, conductive layer material, seed layer material, etc.).

Figure 3D:
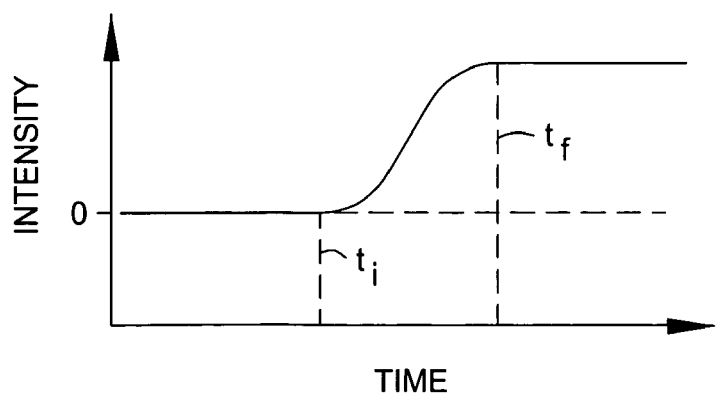
FIG. 3D illustrates a plot of intensity versus time of a measured signal at a wavelength.

In one embodiment the controller 140 is used to monitor the rate of change of intensity of the reflected radiation from the surface of the substrate as a function of time. Using this method the controller can detect the transition of the electroless deposition process into different phases, such as the beginning (e.g., initiation) and the end of the process, by an increase or decrease in the rate of change of the intensity of the reflected radiation at one or more wavelengths. FIG. 3D illustrates a typical plot of the intensity signal measured from the detector 55 as a function of time for a single wavelength of radiation or an average over multiple wavelengths. The intensity's rate of change can be found by calculating the slope of the intensity versus time plot at any instant of time. The rate of change in intensity at one or more wavelengths can be directly related to the electroless deposition rate, even though the relationship of the rate of change of the measured intensity and the deposition rate may not be constant throughout the process. The relationship of the rate of change in intensity and the deposition rate may depend, for example, on the type of materials deposited (e.g., cap layer materials (Cobalt, Cobalt-tungsten-phosphorus, etc.), catalytic layer materials, etc.), a change in roughness of the surface, contamination on the feature surface 26a, or the concentration of certain constituents in the fluid. Since the measurement of the intensity relates to an optical property of the surface of the substrate and not necessarily to the thickness of the deposited film, as compared to other process monitoring techniques (e.g., resistance measurement, eddy current, metapulse techniques, etc.), process characterization steps for different electroless deposition processes are required to correlate the measured intensity signal and the actual state of the deposition process. In a further aspect of the invention, the acceleration or deceleration of the intensity signal (e.g., change in deposition rate), or the rate of change of the rate of change of the intensity signal as a function of time, may be used as an advantage to sense the speeding-up or slowing down of the deposition process to signify a transition to a certain phase (e.g., initiation, etc.) of the deposition process.

In another aspect of the invention, the projected electromagnetic radiation contains wavelengths that are absorbed by components in the deposition fluid. In this embodiment some of the absorbed wavelengths can be used to detect changes in concentration of the electroless deposition fluid components by an increase or decrease in the intensity of the detected radiation. In another embodiment of the present invention a comparison is made between wavelengths that interact (e.g., absorbed, reflected, etc.) with the components in the deposition fluid that are being deposited and also wavelengths that are reflected off the feature surface 26a. In this embodiment the change in the intensity of the wavelength(s) associated with the deposition fluid are intended to monitor the change in concentration of the components that are being deposited. This technique utilizes the system to monitor the growth of the electroless film by use of two process variables in which one is not affected by changes in optical properties of the substrate surface, and when used together can help verify the results obtained from each technique.

As noted above, surface contamination or oxidation has an effect on the time it takes the electroless deposition process to initiate or begin to deposit material. Once the electroless reaction has initiated, the time to deposit a defined amount of material is predictable and will generally fall into a relatively repeatable range of times. Therefore in one embodiment the detection mechanism 60 is used to sense the "initiation" of the electroless deposition process so that the controller can start a timer that will allow the process to run until a defined period of time has lapsed, and thus the end of the process is reached. The amount of time the timer counts before the process is stopped is dependent on the process conditions (e.g., process temperature, concentration of the deposition components, state of the feature surface 26a prior to deposition, fluid agitation, etc.) and the thickness of the deposited material, and is preferably user defined. The magnitude of the user defined process time can be created from data collected from other substrates that are run using similar process conditions and deposition thicknesses. In this mode, after the detection mechanism has sensed the initiation of the reaction, the detection mechanism may or may not monitor the rest of the deposition process. This embodiment can be important for processes where the signal is weak at the end of the process or the signal-to-noise ratio increases towards the end of the process.

In one embodiment the detection mechanism 60 is used to sense the start of the initiation process, a timer is then started, and then by use of the controller 140, the fluid source 128, and the nozzle 123 the substrate 10's surface is rinsed after the defined period of time has lapsed. This embodiment is important in cases where the feature surfaces 26a or the conductive material layer 26 surfaces corrode due to an extended exposure to the deposition fluid. The corrosion of the feature surfaces 26a or the conductive material layer 26 surfaces can affect the electrical properties of the subsequently formed semiconductor device.

One issue that can arise is when the dielectric thickness is rather small and/or the wavelength of electromagnetic radiation is transmitted rather than absorbed by the dielectric material (dielectric material is generally transparent>300 nm) some reflections collected by the detector system 55 may occur from reflective layers below the surface of the substrate. Reflections from surfaces that are not on the top surface may be avoided by careful selection of the emitted and detected wavelengths that are not transmitted through the dielectric layers and by use of signal normalization techniques.

Chamber Hardware

FIG. 5 shows a schematic cross-sectional view of one embodiment of a chamber 160 useful for the deposition of a catalytic layer and/or a conductive material layer as described herein. Of course, the chamber 160 may also be configured to deposit other types of layers other than the catalytic layer and the conductive material layer. The apparatus to electroless deposit the catalytic layer and metallic layers described in the U.S. patent application Ser. No. 10/059,572 [AMAT 5840.03], entitled "Electroless Deposition Apparatus" filed on Jan. 1, 2002 is incorporated by reference herein to the extent not inconsistent with the claimed aspects and disclosure herein. Chamber 160 includes a processing compartment 150 comprising a top 152, sidewalls 154, and a bottom 156. A substrate support 162 is disposed in a generally central location in the chamber 160, and includes a substrate receiving surface 164 adapted to receive a substrate 10 in a face-up position. The chamber 160 further includes a clamp ring 166 configured to hold the substrate 10 against the substrate receiving surface 164. In one aspect, the clamp ring 166 improves the heat transfer between substrate 10 and the heated substrate support 162. Typically the substrate support 162 may heated by use of an external power source and one or more resistive elements embedded in the substrate support 162. In another aspect, the clamp ring 166 holds the substrate during rotation of the substrate support 162. In still another aspect, the thickness of the clamp ring 166 is used to form a pool of deposition fluid 168 on the surface of the substrate 10 during processing.

The chamber 160 further includes a slot 108 or opening formed through a wall thereof to provide access for a robot (not shown) to deliver and retrieve the substrate 10 to and from the chamber 160. Alternatively, the substrate support 162 may raise the substrate 10 through the top 152 of the processing compartment to provide access to and from the chamber 160. The chamber 160 further includes a drain 127 in order to collect and expel fluids used in the chamber 160.

A lift assembly 116 may be disposed below the substrate support 162 and coupled to lift pins 118 to raise and lower lift pins 118 through apertures 120 in the substrate support 162. The lift pins 118 raise and lower the substrate 10 to and from the substrate receiving surface 164 of the substrate support 162. The lift assembly may also be adapted to detach and engage the clamp ring 166 to the surface of substrate 10 to allow the substrate to be clamped to the surface of the substrate support 162 in one case and in another case to allow the substrate 10 to be transferred from the chamber 160.

A motor 1222 may be coupled to the substrate support 162 to rotate the substrate support 162 to spin the substrate 10. In one embodiment, the lift pins 118 may be disposed in a lower position below the substrate support 162 to allow the substrate support 162 to rotate independently of the lift pins 118. In another embodiment, the lift pins 118 may rotate with the substrate support 162.

The substrate support 162 may be heated to heat the substrate 10 to a desired temperature. The substrate receiving surface 164 of the substrate support 162 may be sized to substantially receive the backside of the substrate 10 to provide uniform heating of the substrate 10. Uniform heating of a substrate is an important factor in order to produce consistent processing of substrates, especially for deposition processes having deposition rates that are a function of temperature.

A fluid input, such as a nozzle 123, may be disposed in the chamber 160 to deliver a fluid, such as a chemical processing solution, deionized water, and/or an acid solution, to the surface of the substrate 10. The nozzle 123 may be disposed over the center of the substrate 10 to deliver a fluid to the center of the substrate 10 or may be disposed in any position. The dispense arm 122 may be moveable about a rotatable support member 121 which is adapted to pivot and swivel the dispense arm 122 and the nozzle 123 to and from the center of the substrate 10.

A single or a plurality of fluid sources 128a-f (collectively referred to as "fluid sources") may be coupled to the nozzle 123. Valves 129 may be coupled between the fluid sources 128 and the nozzle 123 to provide a plurality of different types of fluids. Fluid sources 128 may provide, for example and depending on the particular process, deionized water, acid or base solutions, salt solutions, catalytic layer solutions (e.g., noble metal/Group IV metal solutions (i.e. palladium and tin solutions), semi-noble metal/Group IV metal solutions (i.e. cobalt and tin solutions), noble metal solutions, semi-noble metal solutions, Group IV metal solutions), conductive cap layer solutions (e.g., Cobalt (Co), Cobalt-tungsten-phosphorus (CoWP), etc.), reducing agent solutions, and combinations thereof. Preferably, the chemical processing solutions are mixed on an as-needed basis for each substrate 10 that is processed.

The valves 129 may also be adapted to allow a metered amount of fluid to be dispensed to the substrate 10 to minimize chemical waste since some of the chemical processing solutions may be very expensive to purchase and to dispose of.

In an embodiment, where the substrate support 162 is adapted to rotate the rotational speed of the substrate support 162 may be varied according to a particular process being performed (e.g. deposition, rinsing, drying.) In the case of deposition, the substrate support 162 may be adapted to rotate at relatively slow speeds, such as between about 10 RPMs and about 500 RPMs, depending on the viscosity of the fluid, to spread the fluid across the surface of the substrate 10 by virtue of the fluid inertia. In the case of rinsing, the substrate support 162 may be adapted to spin at relatively medium speeds, such as between about 100 RPMs and about 500 RPMs. In the case of drying, the substrate support may be adapted to spin at relatively fast speeds, such as between about 500 RPMS and about 2000 RPMs to spin dry the substrate 10. In one embodiment, the dispense arm 122 is adapted to move during dispensation of the fluid to improve fluid coverage of the substrate 10. Preferably, the substrate support 162 rotates during dispensation of a fluid from the nozzle 123 in order to increase throughput of the system.

The substrate support 162 may include a vacuum port 124 coupled to a vacuum source 125 to supply a vacuum to the backside of the substrate to vacuum chuck the substrate 10 to the substrate support 162. Vacuum Grooves 126 may be formed on the substrate support 162 in communication with the vacuum port 124 to provide a more uniform vacuum pressure across the backside of the substrate 10. In one aspect, the vacuum chuck improves heat transfer between the substrate 10 and the substrate support 162. In addition, the vacuum chuck holds the substrate 10 during rotation of the substrate support 162.

The substrate support 162 may comprise a ceramic material (such as alumina $Al_2O_3$ or silicon carbide (SiC)), TEFLON™ coated metal (such as aluminum or stainless steal), a polymer material, or other suitable materials. The substrate support 162 may further comprise embedded heated elements, especially for a substrate support comprising a ceramic material or a polymer material.

FIG. 5A shows one embodiment where at least one detection mechanism 60, that contains a broadband light source 58, a detection system 55, and a transmissive body 90. The transmissive body 90 is immersed in the pool of deposition fluid 168 formed over the surface of the substrate, thus allowing the radiation emitted from the broadband light source 58 to pass through the transmissive body 90, through the fluid, reflect off the surface of the substrate, pass through the fluid and the transmissive body 90, and be collected by the detection system 55. The transmissive body 90 can be made from, for example, sapphire, quartz, plastic materials or any other optically transparent medium to the emitted radiation. In one embodiment the transmissive body 90 is segmented in two separate bodies (not shown) such that the detection system 55 is in one body and the broadband light source 58 is in the other body. In this embodiment the two bodies are arranged such that the radiation from the broadband light source 58, which is reflected from the surface of the substrate, is collected by the detection system 55. This embodiment can help reduce the mass and size of the device in contact with the deposition fluid 168, thus reducing any possible adverse affects on the deposition process caused by the detection system 60.

Figure 6B:
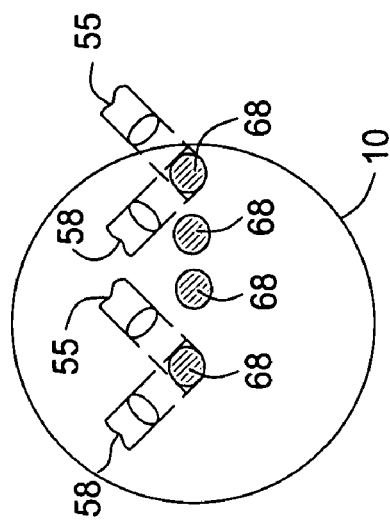
FIG. 6B is a top view of a substrate illustrating one possible array of detection mechanisms distributed across the substrate surface.
Figure 6A:
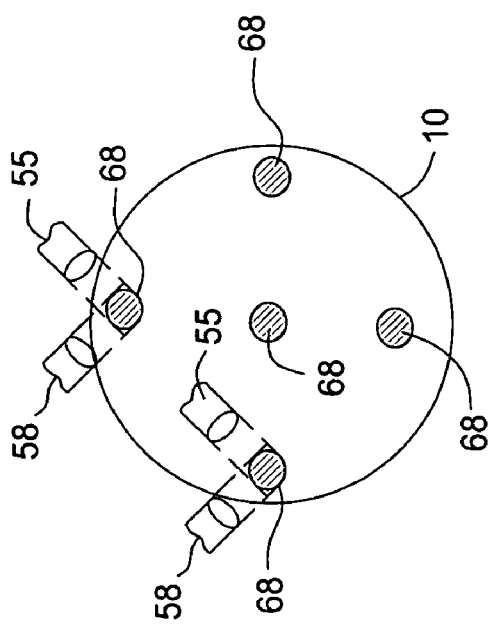
FIG. 6A is a top view of a substrate illustrating one possible array of detection mechanisms distributed across the substrate surface.
Figure 6C:
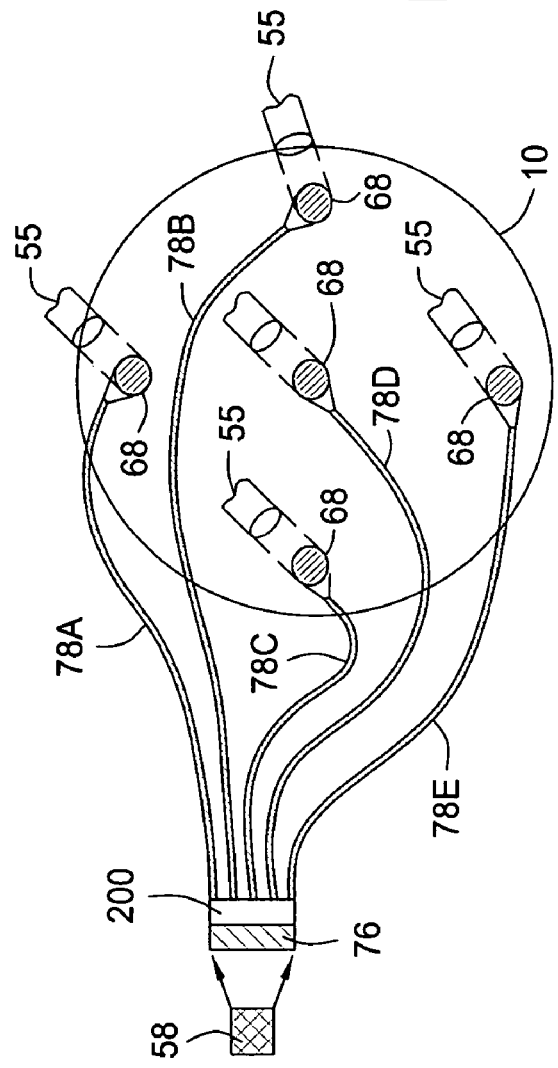
FIG. 6C is a top view of a substrate illustrating one possible array of detection mechanisms distributed across the substrate surface utilizing a single source of electromagnetic radiation.

In one embodiment of the present invention a plurality of the detection mechanisms 60 are spaced in a desired pattern across the surface of the substrate 10 to collect the desired information. FIG. 6A through 6B illustrates exemplary patterns of multiple detection mechanisms 60 are distributed across the surface of the substrate 10 to gain the more information regarding the electroless deposition process. The information gained by the plurality of detection mechanisms 60 is collected in the viewing areas 68 of each of the distributed detectors. In another embodiment, the detection mechanism 60 may include a cluster of receivers and one broadband light source 58. FIG. 6C illustrates a plurality of detector systems 55 and fiber optic cables 78a-e coupled to an optical signal multiplexer 200 that is in communication with the broadband light source 58. The multiplexer 200 is positioned to collect the radiation emitted from the broadband light source 58 and then send the distributed signal to the surface of the substrate. In one embodiment the multiplexer 200 receives the optical data from a monochomator 76 allowing a single light source to effectively deliver a signal at one or more wavelengths to a multitude of inspection sites.

Since it is common to rotate the substrate 10 during processing to improve the electroless deposition process results, it creates a few of complications that lead to a couple of different embodiments of the present invention. In one embodiment the sensors are mounted to the chamber 150, and thus are stationary as the rotating substrate passes under the one or more detection mechanisms 60. In this case the information collected by the detection mechanism 60 tends to average the intensity results over a radial position relative to the center of rotation of the substrate. In this embodiment the radial position of the detection mechanism 60 may be placed at the center of rotation of the substrate, at the outer edge of the substrate, or somewhere in between. In this embodiment the process data collected at one radial position (e.g., center, edge, etc.) may be compared with data collected at another radial position to better quantify any radial variation in the deposition process results.

In another embodiment areas on the surface of the substrate can be compared at one instant of time versus another instant of time by monitoring the angular position of the substrate by use of an encoder (not shown) attached to the motor 1222, and thus comparing the intensity results measured at the same angular position every time it passes the detection mechanism.

In one embodiment, the detection mechanism is attached to an arm mounted to the chamber 150 that can move relative to the surface of the substrate in an effort to scan the surface of the substrate in some predefined pattern (e.g., linear pattern, radial pattern, etc.). By use of one or more position sensors (not shown), a detection mechanism and a controller 140, information regarding the state of the process can be collected at any point on the surface of the substrate as the detector passes over the defined point. Scanning the surface of the substrate can also deliver an average state of the deposition process across the surface of the substrate by summing the intensity values at one or more wavelengths over the scan period and dividing the summed intensity by the time it took to complete the scan.

In yet another embodiment the detection mechanism 60 is designed to rotate with the substrate and is attached to a rotating component, such as the clamp ring 166 or lift assembly (if it rotates with the substrate), to allow the detection mechanism to monitor the change in surface properties at a fixed position on the surface of the rotating substrate. In this embodiment all of the detection mechanism components except, for example, the detector controller 142 and the source controller 141 may be coupled to one or more of the rotating chamber components. The source controller 141 and the detector controller 142 connection to the detection mechanism components can be made through a rotating electrical feed-through commonly known in the art as a slip ring.

In one embodiment, a succession of scans across the same substrate are overlaid to provide a contour map of the substrate. The contour map enhances the process inspection by effectively illustrating changes across the substrate. For example, a substrate having a uniform smooth surface normally would have little change in color variation. A substrate contour map illustrating variations in color may relate to changes in substrate thickness and/or uniformity of the electroless process step.

Face-Down Hardware

Figure 7:
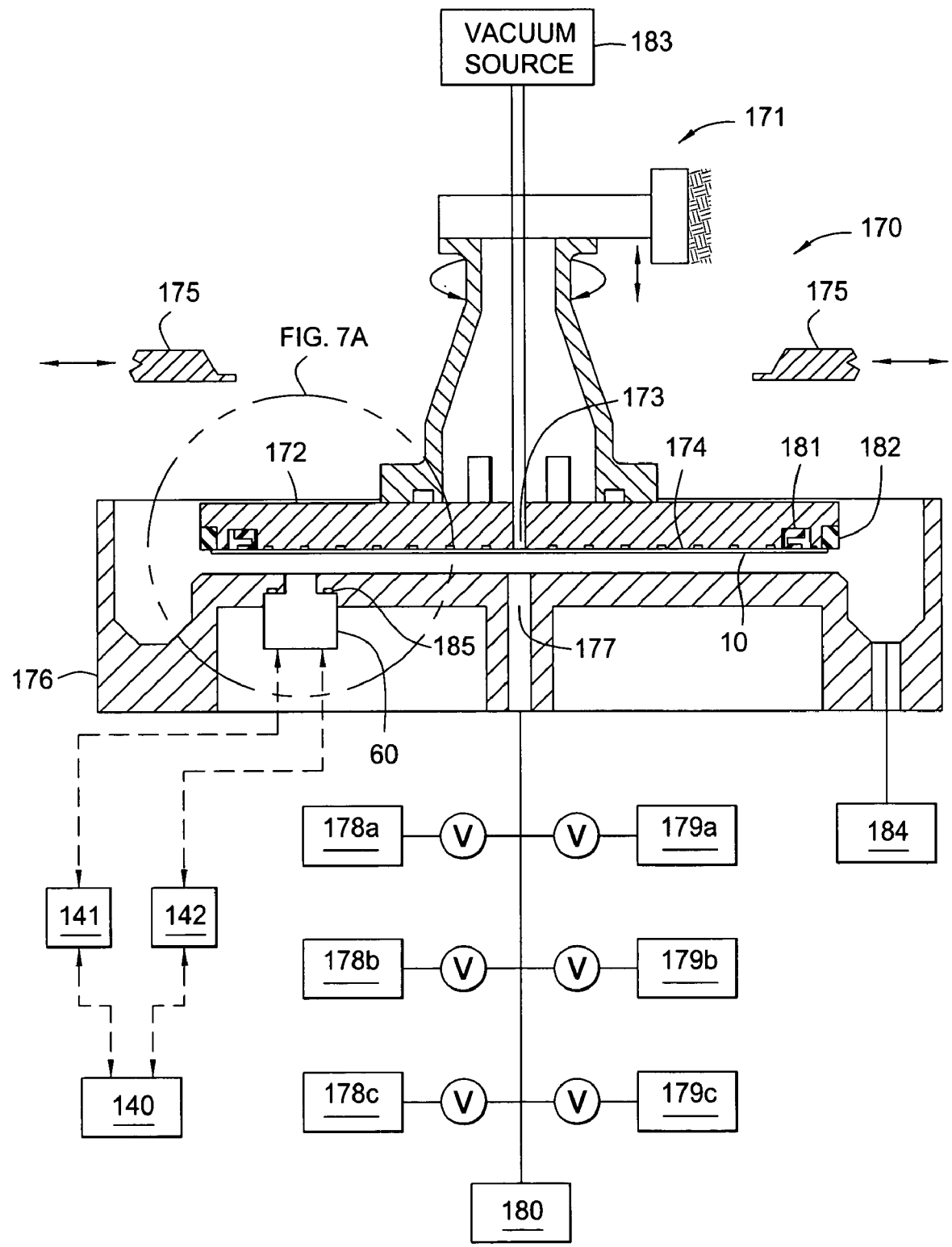
FIG. 7 shows a schematic cross-sectional view of face-down electroless processing chamber used with the present invention.

FIG. 7 shows a schematic cross-sectional view of another embodiment of a chamber 170 useful for the deposition of a catalytic layer and/or a conductive material layer. The chamber 170 includes a substrate holder 172 having a substrate receiving surface 174 adapted to hold a substrate 10 in a face-down position. The substrate holder 172 may be heated to heat the substrate 10 to a desired temperature. The substrate receiving surface 174 of the substrate holder 172 may be sized to substantially receive the backside of the substrate 10 to provide uniform heating of the substrate 10. The substrate holder 172 further includes a vacuum port 173 coupled to a vacuum source 183 to supply a vacuum to the backside of the substrate 10 to vacuum chuck the substrate 10 to the substrate holder 172. The substrate holder 172 may further include a vacuum seal 181 and a liquid seal 182 to prevent the flow of fluid against the backside of the substrate 10 and into the vacuum port 173. The chamber 170 further comprises a bowl 176 having a fluid input, such as a fluid port 177. The fluid port 177 may be coupled to a fluid source 178a-c, a fluid return 179a-b, and/or a gas source 180. In one embodiment a fluid waste drain 184 can be adapted to collect the fluids used during processing.

The substrate holder 172 may further be coupled to a substrate holder assembly 171 adapted to raise and lower the substrate holder 172. In one embodiment, the substrate holder assembly may be adapted to immerse the substrate 10 into a puddle or a bath. In another embodiment, the substrate assembly may be adapted to provide a gap between the substrate 10 and the bowl 176. The fluid source 178 is adapted to provide a fluid through the fluid port 177 to fill the gap between the substrate 10 and the bowl 176 with a fluid layer. In one embodiment a fluid is sprayed onto the surface of the substrate 10 by use of spray or atomizing nozzles (not shown) mounted on the bowl 176 and connected to the fluid source 178a-c. The substrate assembly may be adapted to rotate the substrate holder 172 to provide agitation of the fluid layer.

The bowl 176 may further comprise a heater to heat the fluid layer to a desired temperature. After processing with the fluid layer is complete, the fluid return 179a-c is adapted to pull the fluid back through a drain or the fluid port 177 in order to reclaim the fluid for reuse it in processing other substrates. The gas source 180 is adapted to provide a gas, such as nitrogen, to the surface of the substrate 10 to facilitate drying of the substrate 10. The substrate holder assembly may be further adapted to rotate the substrate holder 172 to spin dry the substrate 10. The chamber 170 may further include a retractable hoop 175 adapted to hold the substrate 10 for transfer from and to the chamber 170. For example, the retractable hoop may include two partial-rings (i.e. each shaped as a "c"). The rings may be moved together to receive a substrate 10. The rings may be move apart to allow the substrate holder 172 to be lowered proximate the bowl 176.

Figure 7A:
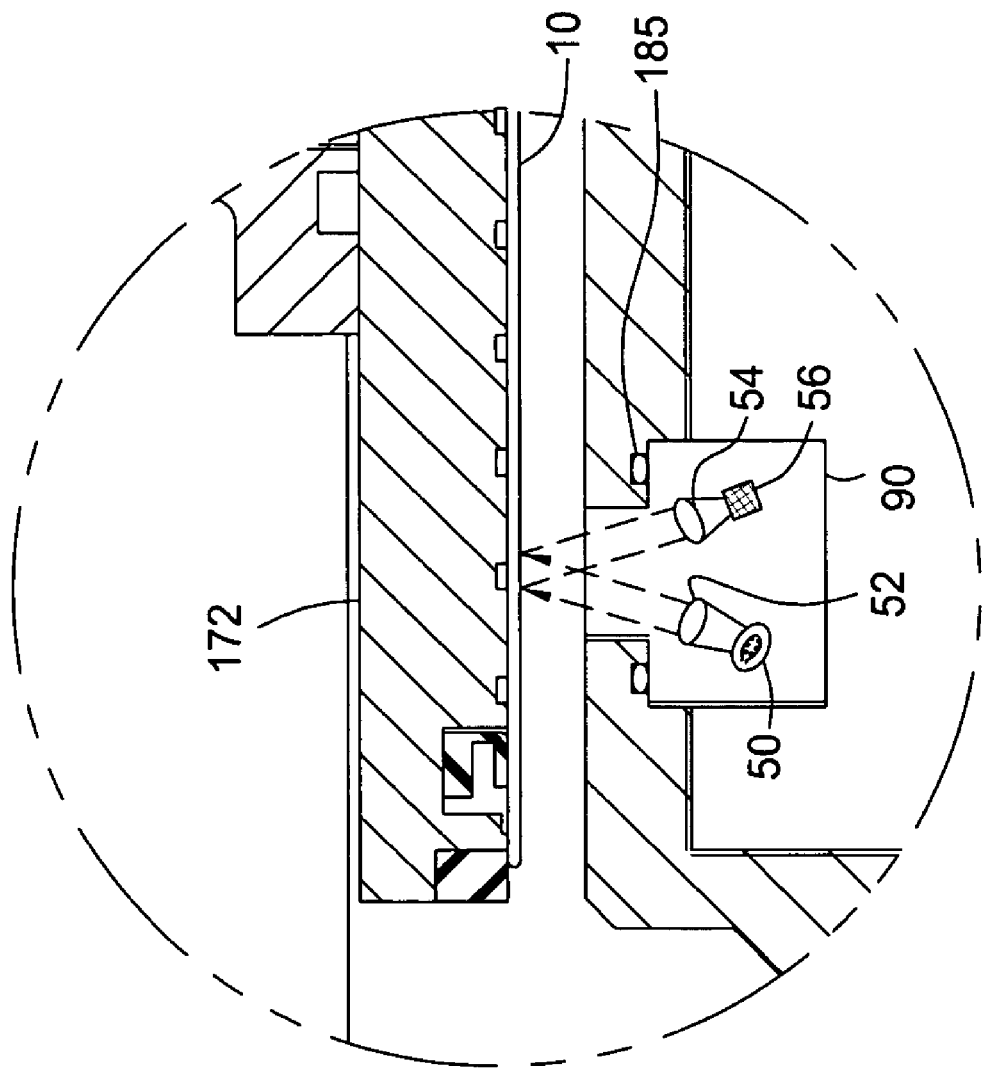
FIG. 7A a close up view of the FIG. 7 showing an embodiment of the present invention.

FIG. 7A shows one embodiment where at least one detection mechanism 60, which contains a broadband light source 58, a detector 55 and a transmissive body 90 is mounted to the bowl 176. The transmissive body 90 is adapted to mount into an area of the bowl 176 that allows it to view the surface of the substrate 10 when in the process position (shown in FIGS. 7 & 7A). The detection mechanism 60 in this embodiment is mounted to the bowl by use of some fastening mechanism (e.g., screws, bolts, adhesive, etc.) and sealed to prevent fluid leakage from the bowl 176 by use of an o-ring seal 185. During processing the transmissive body 90 is immersed in the process fluids, delivered to the chamber via the fluid source 178a-c. In this configuration the projected radiation from the broadband light source 58, passes through the transmissive body 90, through the process fluid, is reflected off the surface of the substrate, passes back through the process fluid and the transmissive body 90, and is finally collected by the detector 55. In one embodiment a plurality of detection mechanisms 60 are spaced in a desired pattern across the surface of the substrate to collect the desired information. Some examples of typical patterns that can be used to maximize the information gathered by the plurality of detection mechanisms 60 similar to those shown in FIGS. 6A through 6B. In one embodiment a detection mechanism 60 scheme that include a cluster of receivers and one light source, similar to the embodiment shown in FIG. 6C described above, which is adapted to suit the face-down processing configuration. As noted above it is common to rotate the substrate 10 during processing to improve the electroless deposition process results for all of the embodiments described in the face up and face down embodiments described above.

The chambers of FIGS. 2-7 may be adapted for the processing of 200 mm substrates, 300 mm substrates, or any sized substrates. The chambers have been shown for single-substrate processing. However, the chambers may be adapted for batch processing. The chambers may be adapted for single use of fluid or may be adapted to recirculate fluids which are reused for a number of substrates and then dumped. For example, in one embodiment, a chamber adapted to recirculate fluids comprises a drain which selectively diverts certain fluids to be reused during processing. If the chamber is adapted to recirculate fluids, the fluid lines should be rinsed in order to prevent deposition in and clogging of the lines. Although the embodiments of the chambers have been described with certain elements and features, it is understood that a chamber may have a combination of elements and features from the different embodiments.

Detection Features

Figure 8:
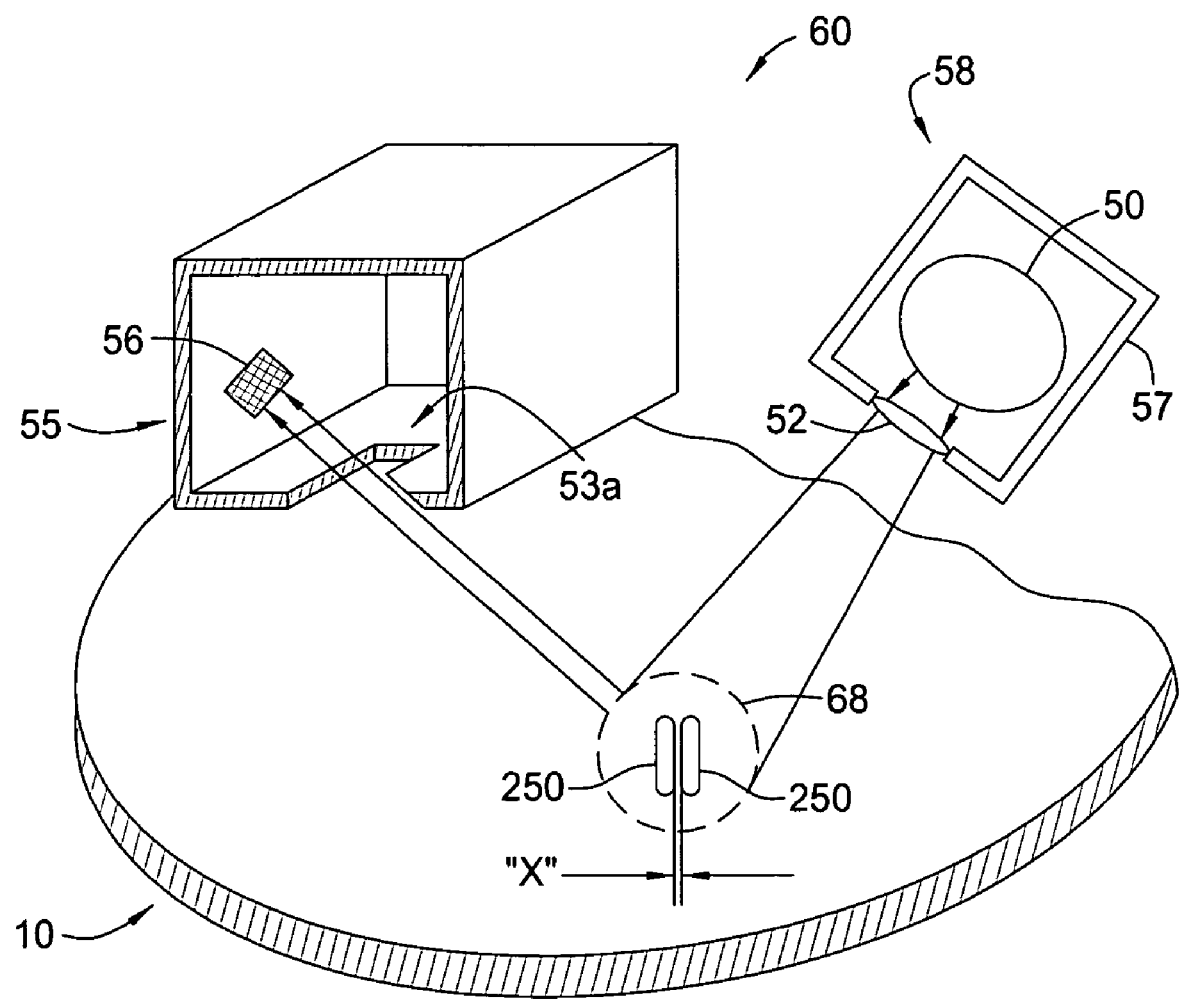
FIG. 8 shows a schematic cross-sectional view of an embodiment of a wafer detection system that utilizes features on the surface of a substrate.

FIG. 8 illustrates one aspect of the present invention in which a plurality of detection features 250 are added to the surface of the substrate to enhance the detection system 60's ability to detect and monitor the electroless deposition process. In this embodiment the detection features 250 generally includes one or more areas on the surface of the substrate that are made from the same metallic materials as the feature surface 26a. The detection features 250 may be added to the "lithographic marks," passive features in a device, or in the "scribe line" commonly found on the surface of semiconductor substrates. It is envisioned that the detection features 250 could be any shape (e.g., circular, oval, rectangular, etc.) and would generally cover an area on the surface of the substrate having a major dimension of between about 100 nanometers and about 100 micrometers in length. In another embodiment the detection features 250 is defined by an array of individual smaller detection features 250 of a size and that are spaced a distance apart (shown as "X") proportional to the desired wavelengths of the projected radiation. The size and spacing of the array of detection features 250 is selected such that the reflected radiation exhibits constructive or destructive interference at one or more wavelengths. In this embodiment growth of the electroless deposited film(s) changes the physical size and spacing of the array of detection features 250 on the surface of the substrate thus altering the wavelengths that exhibit constructive or destructive interference. The change in the reflected wavelengths that exhibit constructive and destructive interference and also the change in intensity at various wavelengths allows the detection system to detect the growth of the deposited film. To reduce any effect of stray light on signal-to-noise ratio it is likely that the detector system 60 and the viewing area 68 on the surface of the substrate need to be covered or shielded from any ambient light sources. A slit, narrow aperture (opening 53a), may also be added to the detector system 55 to control the amount of radiation collected by the detector to enhance the detection process and improve the signal-to-noise ratio.

Figure 9B:
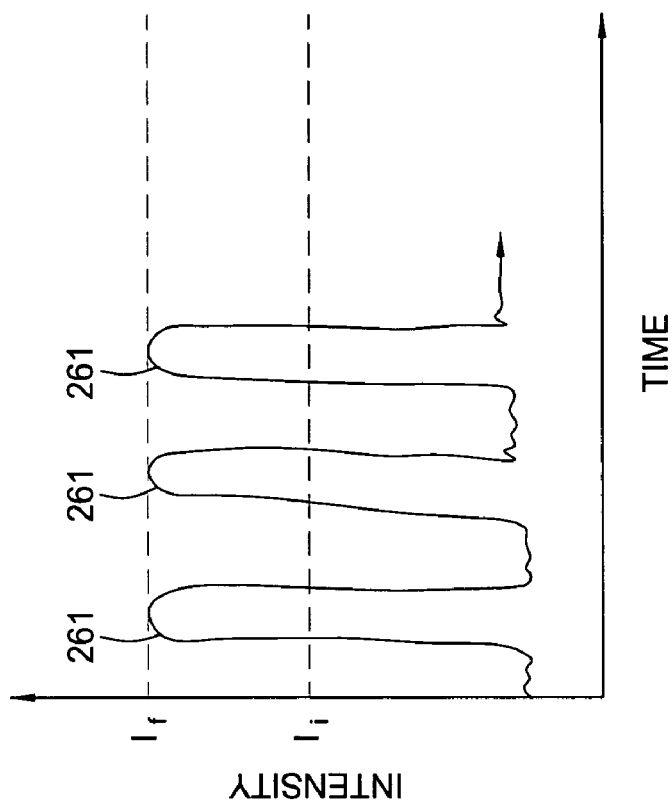
FIG. 9B illustrates a plot of intensity versus time measured by the detector system of FIG. 9A as substrate 10 is rotated at a second time.
Figure 9A:
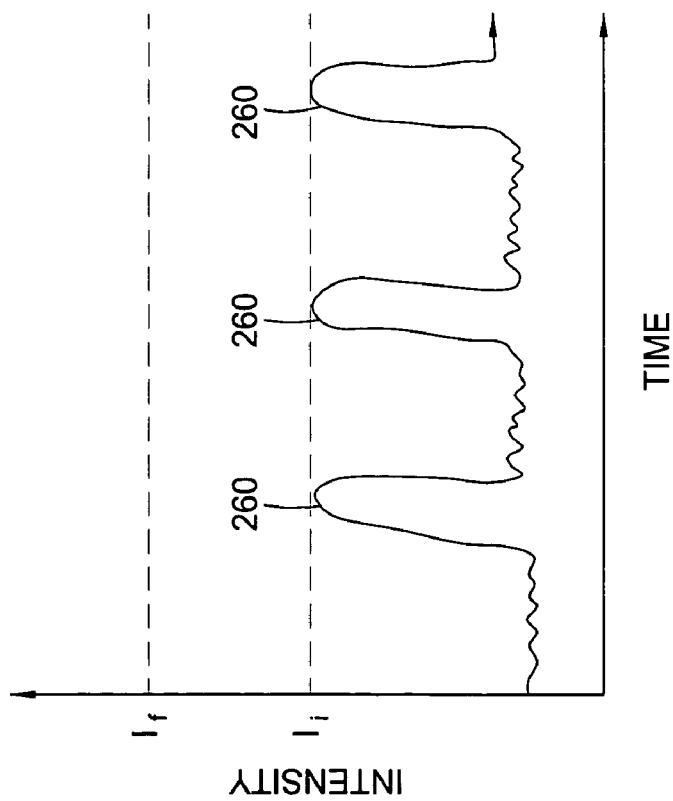
FIG. 9A illustrates a plot of intensity versus time measured by a detector system as substrate 10 is rotated at a first time.

In another embodiment the substrate 10 is moved relative to the detector system 60 such that one or more arrays of (or a single) detection features 250 pass through the viewing area 68 of the detection system 60 at some regular interval of time. By knowing the interval of time with which the detection features pass through the viewing area and monitoring the intensity of the radiation collected by the detection system 60 the controller can sense a change intensity of reflected radiation from the surface of the various arrays of detection features 250. The endpoint of the deposition process is found when the intensity change from a first time (shown in FIG. 9A) versus a second time (shown in FIG. 9B) reaches some user defined process or programmed value. FIG. 9A illustrates an example of a typical intensity versus time plot, detected by the detection system 60 and monitored by the system controller 140 every time the detection features 250 pass through the viewing area 68, at some time early in the deposition process. FIG. 9B illustrates an example of a typical intensity versus time plot, detected by the detection system 60 and monitored by the system controller 140 every time the detection features 250 pass through the viewing area 68, at some time after the deposition process has started. Comparing the illustrative data shown FIGS. 9A and 9B the system controller 140 would note an increase in the signal intensity (first intensity data 260<second intensity data 261) at two different times during the process and reacts according to the user defined rules contained in the system controller 140.

While the foregoing is directed to embodiments of the present invention, other and further embodiments of the invention may be devised without departing from the basic scope thereof, and the scope thereof is determined by the claims that follow.

The invention claimed is:

1. An apparatus for monitoring an electroless deposition process performed on a substrate comprising:
   a chamber;
   a substrate support disposed in the chamber and having a substrate receiving surface;
   an electromagnetic radiation source directed towards the substrate receiving surface;
   a detector that detects the intensity of reflected electromagnetic radiation from a surface of the substrate when disposed on the substrate receiving surface during the electroless deposition process;
   an emission sensor adapted to measure and compare an output of the electromagnetic radiation source with the reflected electromagnetic radiation collected by the detector;
   a fluid source that is adapted to deliver an electroless plating solution to the surface of the substrate when the substrate is disposed on the substrate receiving surface; and
   a controller adapted to receive a signal from the detector and a signal from the emission sensor.

2. The apparatus of claim 1, wherein the electromagnetic radiation source emits electromagnetic radiation at wavelengths between about 200 nanometers and about 800 nanometers.

3. The apparatus of claim 1, wherein the electromagnetic radiation source comprises one or more light emitting diodes.

4. The apparatus of claim 1, wherein the detector comprises two or more detectors.

5. The apparatus of claim 1, further comprising a drive mechanism to move the substrate support relative to the detector.

6. An apparatus of claim 5, further comprising a second drive mechanism to move the detector relative to the substrate support.

7. The apparatus of claim 1, wherein the detector is a spectrometer.

8. The apparatus of claim 1, wherein the electroless plating solution comprises a catalytic layer solution, a semi-noble metal solution, a noble metal solution, or a conductive cap layer solution.

9. The apparatus of claim 1, wherein the controller further comprises:
   a timer that is adapted to define when a desired period of time has lapsed; and
   a rinsing fluid source that is adapted to deliver a rinsing solution to the surface of the substrate after the desired period of time has lapsed.

10. An apparatus for monitoring an electroless deposition process performed on a substrate comprising:
    a chamber;
    a substrate support disposed in the chamber and having a substrate receiving surface;
    an electromagnetic radiation source directed towards the substrate receiving surface;

a detector that detects the intensity of reflected electromagnetic radiation from a surface of the substrate when disposed on the substrate receiving surface during the electroless deposition process;
a controller adapted to receive a signal from the detector and to control the electroless deposition process;
a fiber optic cable which receives the electromagnetic radiation collected from the electromagnetic radiation source;
a mechanical slit that allows the reflected electromagnetic radiation or the electromagnetic radiation from the fiber optic cable to pass to the detector; and
a controller that selectively controls the transmission of the reflected electromagnetic radiation or the electromagnetic radiation from the fiber optic cable to the detector by use of a mechanical actuator that positions the mechanical slit.

11. An apparatus for monitoring an electroless deposition process performed on a substrate comprising:
a chamber;
a substrate support disposed in the chamber and having a substrate receiving surface;
an electromagnetic radiation source directed towards the substrate receiving surface;
a detector that detects the intensity of reflected electromagnetic radiation from a surface of the substrate when disposed on the substrate receiving surface during the electroless deposition process;
a controller adapted to receive a signal from the detector and to control the electroless deposition process;
a memory attached to the controller to stored the signal data; and
a control device wherein the controller device is used to control the electroless deposition process based on commands from the controller based on the comparison of the signal data and a process value.

12. An apparatus for monitoring an electroless deposition process performed on a substrate comprising:
a chamber;
a substrate support disposed in the chamber and having a substrate receiving surface;
an electromagnetic radiation source directed towards the substrate receiving surface;
a detector that detects the intensity of the reflected electromagnetic radiation from a surface of the substrate when disposed on the substrate receiving surface during the electroless deposition process;
a second detector that detects the intensity of the electromagnetic radiation from the electromagnetic radiation source;
a controller adapted to receive a signal from the detector and a signal from the second detector and to control the electroless deposition process; and
a fiber optic cable that receives the electromagnetic radiation collected from the electromagnetic radiation source and transmits the signal to the second detector.

13. The apparatus of claim 12, wherein the detector is a spectrometer.

14. The apparatus of claim 12, wherein the electromagnetic radiation source emits electromagnetic radiation at wavelengths between about 200 nanometers and about 800 nanometers.

15. The apparatus of claim 12, wherein the detector comprises two or more detectors.

16. The apparatus of claim 12, further comprising a drive mechanism to can move the substrate support relative to the detector.

17. An apparatus of claim 16, further comprising a second drive mechanism to move the detector relative to the substrate support.

18. The apparatus of claim 12, wherein the second detector is a spectrometer.

19. The apparatus of claim 12, wherein the electromagnetic radiation source is one or more light emitting diodes.

20. An apparatus for monitoring an electroless deposition process performed on a substrate comprising:
a chamber;
a substrate support disposed in the chamber and having a substrate receiving surface;
a electromagnetic radiation source directed towards the substrate receiving surface;
a detector that detects the intensity of the reflected electromagnetic radiation from a surface of the substrate when disposed on the substrate receiving surface during the electroless deposition process;
a fluid source that is adapted to deliver an electroless plating solution to the surface of the substrate when it is disposed on the substrate receiving surface; and
a controller adapted to receive a signal from the detector, and is adapted to start a timer when the detected intensity of the reflected electromagnetic radiation reaches a desired value and end an electroless process step when the timer has reached a desired value.

21. The apparatus of claim 20, wherein the electroless plating solution comprises a catalytic layer solution, a semi-noble metal solution, a noble metal solution, or a conductive cap layer solution.

22. The apparatus of claim 20, wherein electromagnetic radiation source further comprises one or more light emitting diodes.

23. The apparatus of claim 20, further comprising a rinsing fluid source that is adapted to deliver a rinsing solution to the surface of the substrate.

24. An apparatus for monitoring an electroless deposition process performed on a substrate comprising:
a chamber;
a substrate support disposed in the chamber and having a substrate receiving surface;
a electromagnetic radiation source comprising one or more light emitting diodes directed towards the substrate receiving surface;
a detector that detects the intensity of the reflected electromagnetic radiation from a surface of the substrate when disposed on the substrate receiving surface during the electroless deposition process;
a controller adapted to receive a signal from the detector and processes the signals to determine an initiation of the electroless deposition process; and
a second detector that detects the intensity of the electromagnetic radiation from the electromagnetic radiation source.

25. A system for monitoring an electroless deposition process performed on a substrate comprising:
a chamber;
a substrate support mounted in the chamber and having a substrate receiving surface;
an electromagnetic radiation source directed towards the substrate receiving surface;
a detector that detects the intensity of the reflected electromagnetic radiation from a surface of the substrate when disposed on the substrate receiving surface during the electroless deposition process;
a controller adapted to receive a signal from the detector and to control the electroless deposition process; and a memory, coupled to the controller, the memory comprising a computer-readable medium having a computer-readable program embodied therein for directing the operation of the electroless deposition system, the computer-readable program comprising:
computer instructions to control the electroless deposition system to:
i. start processing;
ii. collect and store into the memory the intensity of the reflected electromagnetic radiation data during the electroless deposition process;
iii. compare the stored data with the collected data, then subsequently;
iv. stop the electroless deposition process when the collected data exceeds a threshold value.

26. The apparatus of claim 25, wherein the threshold value data is stored in the memory.

27. The apparatus of claim 25, wherein the electromagnetic radiation source emits electromagnetic radiation at wavelengths between about 200 nanometers and about 800 nanometers.

28. The apparatus of claim 25, wherein the electromagnetic radiation source is one or more light emitting diodes.

29. The apparatus of claim 25, wherein the detector comprises two or more detectors.

30. The apparatus of claim 25, further comprising a drive mechanism to can move the substrate support relative to the detector.

31. An apparatus of claim 30, further comprising a second drive mechanism to move the detector relative to the substrate support.

32. The apparatus of claim 25, wherein the detector is a spectrometer.

33. The apparatus of claim 25, further comprising a second detector that detects the intensity of the electromagnetic radiation from the electromagnetic radiation source.

34. An apparatus for monitoring an electroless deposition process performed on a substrate comprising:
a chamber;
a substrate support disposed in the chamber and having a substrate receiving surface;
the substrate having a detection feature on a surface, wherein the substrate is disposed on the substrate receiving surface of the substrate support;
an electromagnetic radiation source directed towards the surface of the substrate;
a detector that detects the intensity of reflected electromagnetic radiation from the detection feature during the electroless deposition process, wherein the detection feature comprises two or more metallic features disposed on the surface of the substrate;
an emission sensor adapted to measure and compare an output of the electromagnetic radiation source with the reflected electromagnetic radiation collected by the detector;
a fluid source that is adapted to deliver an electroless plating solution to the surface of the substrate when the substrate is disposed on the substrate receiving surface; and
a controller adapted to receive a signal from the detector and a signal from the emission sensor, and to control the electroless deposition process.

35. The apparatus of claim 34, wherein the electromagnetic radiation source emits electromagnetic radiation at wavelengths between about 200 nanometers and about 800 nanometers.

36. The apparatus of claim 34, wherein the detection feature is shaped to interact with the electromagnetic radiation reflected from the detection feature as the electroless deposition process progresses.

37. The apparatus of claim 34, wherein the electromagnetic radiation source comprises one or more light emitting diodes.

38. The apparatus of claim 34, wherein the detector comprises two or more detectors.

39. The apparatus of claim 34, further comprising a drive mechanism to move the substrate support relative to the detector.

40. An apparatus of claim 39, further comprising a second drive mechanism to move the detector relative to the substrate support.

41. The apparatus of claim 34, wherein the detector is a spectrometer.

42. The apparatus of claim 34, wherein the detection feature is an array of features spaced between about 100 nanometers and about 100 micrometers apart.

43. The apparatus of claim 34, wherein the electroless plating solution comprises a catalytic layer solution, a semi-noble metal solution, a noble metal solution, or a conductive cap layer solution.

44. An apparatus for monitoring an electroless deposition process performed on a substrate comprising:
a chamber;
a substrate support disposed in the chamber and having a substrate receiving surface;
a electromagnetic radiation source directed towards the substrate receiving surface;
a detector that detects the intensity of the reflected electromagnetic radiation from a surface of the substrate when disposed on the substrate receiving surface during the electroless deposition process;
a fluid source that is adapted to deliver an electroless plating solution to the surface of the substrate when it is disposed on the substrate receiving surface;
a motor coupled to the substrate support, wherein the motor is adapted to rotate the substrate receiving surface; and
a controller adapted to receive a signal from the detector, wherein the controller is adapted to control the rotation of the substrate receiving surface after the detected intensity of the reflected electromagnetic radiation from the surface of the substrate reaches a desired value.

45. The apparatus of claim 44 wherein the electroless plating solution comprises a catalytic layer solution, a semi-noble metal solution, a noble metal solution, or a conductive cap layer solution.

46. The apparatus of claim 44, further comprising a rinsing fluid source that is adapted to deliver a rinsing solution to the surface of the substrate.

* * * * *